(12) United States Patent
Patel et al.

(10) Patent No.: US 8,521,281 B2
(45) Date of Patent: Aug. 27, 2013

(54) ELECTROGRAM CLASSIFICATION ALGORITHM

(75) Inventors: Amisha S. Patel, Maple Grove, MN (US); Jian Cao, Shoreview, MN (US); Karen J. Kleckner, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 60 days.

(21) Appl. No.: 13/273,962

(22) Filed: Oct. 14, 2011

(65) Prior Publication Data

US 2013/0096449 A1 Apr. 18, 2013

(51) Int. Cl.
*A61N 1/362* (2006.01)

(52) U.S. Cl.
USPC ............................. 607/14; 607/30

(58) Field of Classification Search
USPC .................................. 607/9, 14, 30
See application file for complete search history.

(56) References Cited

U.S. PATENT DOCUMENTS

| | | | |
|---|---|---|---|
| 4,140,131 A | 2/1979 | Dutcher et al. |
| 4,374,382 A | 2/1983 | Markowitz |
| 4,428,378 A | 1/1984 | Anderson et al. |
| 4,549,548 A | 10/1985 | Wittkampf et al. |
| 4,825,869 A | 5/1989 | Sasmor et al. |
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |
| 5,137,021 A | 8/1992 | Wayne et al. |
| 5,168,871 A | 12/1992 | Grevious |
| 5,184,614 A | 2/1993 | Collins et al. |
| 5,193,535 A | 3/1993 | Bardy et al. |
| 5,193,550 A | 3/1993 | Duffin |
| 5,201,865 A | 4/1993 | Kuehn |
| 5,215,081 A | 6/1993 | Ostroff |
| 5,224,475 A | 7/1993 | Berg et al. |
| 5,226,415 A | 7/1993 | Girodo et al. |

(Continued)

FOREIGN PATENT DOCUMENTS

WO 2009111766 A2 9/2009

OTHER PUBLICATIONS

U.S. Appl. No. 12/837,320, by Hendrikus A. Westendorp, filed Jul. 15, 2010.

(Continued)

*Primary Examiner* — George Evanisko
(74) *Attorney, Agent, or Firm* — Michael C. Soldner

(57) ABSTRACT

The present disclosure is directed to the classification of cardiac episodes using an algorithm. In various examples, an episode classification algorithm evaluates electrogram signal data using a probabilistic ventricular oversensing algorithm. The algorithm may look at a plurality of factors weighing for and against a determination of ventricular oversensing. In some examples, the algorithm may also determine whether the cardiac episode includes atrial sensing issues.

29 Claims, 13 Drawing Sheets

(56) References Cited

U.S. PATENT DOCUMENTS

| | | |
|---|---|---|
| 5,292,343 A | 3/1994 | Blanchette et al. |
| 5,312,441 A | 5/1994 | Mader et al. |
| 5,314,450 A | 5/1994 | Thompson |
| 5,324,315 A | 6/1994 | Grevious |
| 5,354,319 A | 10/1994 | Wyborny et al. |
| 5,379,776 A | 1/1995 | Murphy et al. |
| 5,381,803 A | 1/1995 | Herleikson et al. |
| 5,383,909 A | 1/1995 | Keimel |
| 5,411,530 A | 5/1995 | Akhtar |
| 5,431,692 A | 7/1995 | Hansen et al. |
| 5,462,060 A | 10/1995 | Jacobson et al. |
| 5,507,746 A | 4/1996 | Lin |
| 5,507,786 A | 4/1996 | Morgan et al. |
| 5,509,927 A | 4/1996 | Epstein et al. |
| 5,527,344 A | 6/1996 | Arzbaecher et al. |
| 5,534,018 A | 7/1996 | Wahlstrand et al. |
| 5,545,183 A | 8/1996 | Altman |
| 5,545,186 A | 8/1996 | Olson et al. |
| 5,549,646 A | 8/1996 | Katz et al. |
| 5,558,098 A | 9/1996 | Fain |
| 5,564,434 A | 10/1996 | Halperin et al. |
| 5,660,183 A | 8/1997 | Chiang et al. |
| 5,707,398 A | 1/1998 | Lu |
| 5,722,997 A | 3/1998 | Nedungadi et al. |
| 5,722,999 A | 3/1998 | Snell |
| 5,730,141 A | 3/1998 | Fain et al. |
| 5,741,311 A | 4/1998 | Mc Venes et al. |
| 5,755,735 A | 5/1998 | Richter et al. |
| 5,755,736 A | 5/1998 | Gillberg et al. |
| 5,755,739 A | 5/1998 | Sun et al. |
| 5,755,742 A | 5/1998 | Schuelke et al. |
| 5,776,168 A | 7/1998 | Gunderson |
| 5,814,088 A | 9/1998 | Paul et al. |
| 5,868,793 A | 2/1999 | Nitzsche et al. |
| 5,891,170 A | 4/1999 | Nitzsche et al. |
| 5,891,179 A | 4/1999 | Er et al. |
| 5,897,577 A | 4/1999 | Cinbis et al. |
| 5,910,156 A | 6/1999 | Cinbis et al. |
| 5,944,746 A | 8/1999 | Kroll |
| 6,067,473 A | 5/2000 | Greeninger et al. |
| 6,070,097 A | 5/2000 | Kreger et al. |
| 6,085,118 A | 7/2000 | Hirschberg et al. |
| 6,112,119 A | 8/2000 | Schuelke et al. |
| 6,129,745 A | 10/2000 | Sun et al. |
| 6,129,746 A | 10/2000 | Levine et al. |
| 6,141,585 A | 10/2000 | Prutchi et al. |
| 6,155,267 A | 12/2000 | Nelson |
| 6,169,923 B1 | 1/2001 | Kroll |
| 6,266,554 B1 | 7/2001 | Hsu et al. |
| 6,270,457 B1 | 8/2001 | Bardy |
| 6,317,632 B1 | 11/2001 | Krig et al. |
| 6,317,633 B1 | 11/2001 | Jorgenson et al. |
| 6,358,203 B2 | 3/2002 | Bardy |
| 6,393,316 B1 | 5/2002 | Gillberg et al. |
| 6,434,428 B1 | 8/2002 | Sloman et al. |
| 6,445,952 B1 | 9/2002 | Manrodt et al. |
| 6,470,210 B1 | 10/2002 | Chen et al. |
| 6,477,417 B1 | 11/2002 | Levine |
| 6,493,586 B1 | 12/2002 | Stahmann et al. |
| 6,599,250 B2 | 7/2003 | Webb et al. |
| 6,607,485 B2 | 8/2003 | Bardy |
| 6,629,931 B1 | 10/2003 | Begemann et al. |
| 6,650,931 B1 | 11/2003 | McClure et al. |
| 6,658,294 B1 | 12/2003 | Zadeh et al. |
| 6,669,631 B2 | 12/2003 | Norris et al. |
| 6,721,600 B2 | 4/2004 | Jorgenson et al. |
| 6,748,269 B2 | 6/2004 | Thompson et al. |
| 6,760,624 B2 | 7/2004 | Anderson et al. |
| 6,788,971 B1 | 9/2004 | Sloman et al. |
| 6,865,141 B2 | 3/2005 | Tada et al. |
| 6,974,413 B2 | 12/2005 | Bardy |
| 6,980,860 B2 | 12/2005 | Stadler et al. |
| 7,047,083 B2 | 5/2006 | Gunderson et al. |
| 7,069,085 B2 | 6/2006 | Cao et al. |
| 7,167,747 B2 | 1/2007 | Gunderson et al. |
| 7,206,633 B2 | 4/2007 | Saba |
| 7,212,849 B2 | 5/2007 | Zhang et al. |
| 7,236,828 B2 | 6/2007 | Casavant et al. |
| 7,266,409 B2 | 9/2007 | Gunderson |
| 7,286,997 B2 | 10/2007 | Spector et al. |
| 7,289,851 B2 | 10/2007 | Gunderson et al. |
| 7,333,855 B2 | 2/2008 | Gunderson et al. |
| 7,353,063 B2 | 4/2008 | Simms, Jr. |
| 7,369,893 B2 | 5/2008 | Gunderson |
| 7,430,446 B2 | 9/2008 | Li |
| 7,480,529 B2 | 1/2009 | Li |
| 7,539,540 B2 | 5/2009 | Gunderson et al. |
| 7,567,835 B2 | 7/2009 | Gunderson et al. |
| 7,582,061 B2 | 9/2009 | Li et al. |
| 7,738,950 B2 | 6/2010 | Johnson et al. |
| 7,894,883 B2 | 2/2011 | Gunderson et al. |
| 7,974,690 B2 | 7/2011 | Kracker |
| 2001/0007053 A1 | 7/2001 | Bardy |
| 2001/0031997 A1 | 10/2001 | Lee |
| 2001/0037366 A1 | 11/2001 | Webb et al. |
| 2002/0091333 A1 | 7/2002 | Hsu et al. |
| 2002/0116031 A1 | 8/2002 | Vonk |
| 2002/0118215 A1 | 8/2002 | Ball et al. |
| 2002/0120307 A1 | 8/2002 | Jorgenson et al. |
| 2003/0050563 A1 | 3/2003 | Suribhotla et al. |
| 2003/0060849 A1 | 3/2003 | Hsu |
| 2003/0074026 A1 | 4/2003 | Thompson et al. |
| 2003/0204146 A1 | 10/2003 | Carlson |
| 2003/0204215 A1 | 10/2003 | Gunderson et al. |
| 2004/0015197 A1 | 1/2004 | Gunderson et al. |
| 2004/0064161 A1 | 4/2004 | Gunderson et al. |
| 2004/0088018 A1 | 5/2004 | Sawchuk et al. |
| 2004/0093240 A1 | 5/2004 | Shah |
| 2004/0106955 A1 | 6/2004 | Swerdlow et al. |
| 2004/0122487 A1 | 6/2004 | Hatlestad et al. |
| 2004/0186388 A1 | 9/2004 | Gerasimov |
| 2004/0220631 A1 | 11/2004 | Burnes et al. |
| 2004/0230233 A1 | 11/2004 | Gunderson et al. |
| 2004/0230242 A1 | 11/2004 | van Dam et al. |
| 2005/0022181 A1 | 1/2005 | Fox et al. |
| 2005/0049910 A1 | 3/2005 | Lancaster et al. |
| 2005/0060193 A1 | 3/2005 | Lancaster et al. |
| 2005/0075902 A1 | 4/2005 | Wager et al. |
| 2005/0080347 A1 | 4/2005 | Sheth et al. |
| 2005/0137636 A1 | 6/2005 | Gunderson et al. |
| 2005/0154421 A1 | 7/2005 | Ousdigian |
| 2005/0159785 A1 | 7/2005 | Rueter |
| 2005/0192506 A1 | 9/2005 | Kim et al. |
| 2005/0192836 A1 | 9/2005 | Rossinni et al. |
| 2005/0192844 A1 | 9/2005 | Esler et al. |
| 2006/0064020 A1 | 3/2006 | Burnes et al. |
| 2006/0074331 A1 | 4/2006 | Kim et al. |
| 2006/0074454 A1 | 4/2006 | Freeberg |
| 2006/0074464 A1 | 4/2006 | Subera et al. |
| 2006/0116596 A1 | 6/2006 | Zhou et al. |
| 2006/0116732 A1 | 6/2006 | Gunderson et al. |
| 2006/0116733 A1 | 6/2006 | Gunderson |
| 2006/0217621 A1 | 9/2006 | Kim et al. |
| 2006/0217769 A1 | 9/2006 | Saba |
| 2006/0224075 A1 | 10/2006 | Gunderson |
| 2006/0235476 A1 | 10/2006 | Gunderson et al. |
| 2006/0281998 A1 | 12/2006 | Li |
| 2007/0061393 A1 | 3/2007 | Moore |
| 2007/0123788 A1 | 5/2007 | Gunderson et al. |
| 2007/0123789 A1 | 5/2007 | Gunderson et al. |
| 2007/0123790 A1 | 5/2007 | Gunderson et al. |
| 2007/0123941 A1 | 5/2007 | Gunderson et al. |
| 2007/0135863 A1 | 6/2007 | Gunderson et al. |
| 2007/0135864 A1 | 6/2007 | Gunderson et al. |
| 2008/0082012 A1 | 4/2008 | Gunderson et al. |
| 2008/0161870 A1 | 7/2008 | Gunderson |
| 2008/0161872 A1 | 7/2008 | Gunderson |
| 2010/0145404 A1 | 6/2010 | Rouw et al. |
| 2010/0211125 A1 | 8/2010 | Johnson et al. |
| 2010/0249627 A1 | 9/2010 | Zhang |
| 2010/0274146 A1 | 10/2010 | Li et al. |
| 2011/0098764 A1 | 4/2011 | Sloman |
| 2011/0098766 A1 | 4/2011 | Gunderson |
| 2011/0112417 A1* | 5/2011 | Gunderson et al. .......... 600/509 |

OTHER PUBLICATIONS

U.S. Appl. No. 13/274,010, by Amisha S. Patel, filed Oct. 14, 2011.
Office Action from U.S. Appl. No. 13/274,010, dated Mar. 6, 2013, 12 pp.

(PCT/US2012/059449) PCT Notification of Transmittal of the International Search Report and the Written Opinion of the International Searching Authority.

* cited by examiner though the atrial sensing issues are repairable; in response to a determination that the atrial sensing issues are repairable, repair the sensing issues and classify the cardiac episode based on a set of classification rules that consider both the ventricular and atrial sensed events; in response to a determination that the atrial sensing issues are not repairable, classify the cardiac episode based on at least one classification rule that considers the ventricular sensed events but not the atrial sensed events; and wherein the classification comprises ventricular tachycardia/ventricular fibrillation, inappropriately shocked, or indeterminate.

ELECTROGRAM CLASSIFICATION ALGORITHM

TECHNICAL FIELD

The disclosure relates to algorithms for classifying cardiac episodes detected by an implantable medical device (IMD).

BACKGROUND

Some implantable medical devices (IMDs) monitor physiological parameters or signals of the patients within which they are implanted. Such implantable medical devices may detect episodes based on the monitoring. An IMD may store a variety of data regarding detected episodes, and a clinician may retrieve the episode data from the IMD for diagnosing the patient and/or confirming the accuracy of the detection of the episodes by the IMD. For example, implantable cardioverter-defibrillators (ICDs) may detect cardiac episodes, such as tachyarrhythmia episodes, based on monitoring cardiac electrogram signals and, in some cases, additional physiological signals or parameters. A clinician may review the data stored by the ICD for the episodes to confirm that accuracy of the diagnosis of tachyarrhythmia by the ICD.

As the memory capacity and diagnostic capabilities of IMDs, such as ICDs, increases, the amount of time required to adequately review the retrieved data to determine whether the detection of episodes and delivery of therapy by the device was appropriate also increases. Manual review of episodes may be challenging because of the number of patients a clinician follows, an increase in the total number of episodes to review and the significant level of expertise required. Additionally, the time available for clinicians with expertise to review each episode has been reduced. This may result in a reduction in the quality of management of those patients having implanted devices.

Automated algorithms for post-processing cardiac episodes previously detected by ICDs have been proposed to address these concerns. Such algorithms generally evaluate the cardiac electrogram and other data stored by an ICD for an episode to provide an independent classification of the episode. The post-processing classification may be compared to the classification made by the ICD to determine the accuracy of the classification by the ICD. Such algorithms may potentially suggest ICD parameter changes and/or changes to medical therapy, such as changes in medication, therapy delivery, use of ablation procedures, etc. One algorithm for automated algorithms for post-processing of cardiac episodes is disclosed in U.S. Pat. No. 7,894,883 to Gunderson et al., which is incorporated herein by reference in its entirety.

SUMMARY

In general, the present disclosure is directed to using an algorithm to analyze an electrogram (EGM) signal to provide a classification of a cardiac episode based at least in part on a probabilistic analysis of ventricular oversensing (VOS). The probabilistic analysis of VOS looks for the presence of a variety of factors that may weigh for or against a finding of VOS. At least a first factor is given a different weight than a second factor. In some examples, the algorithm detects atrial sensing issues.

In one example, the disclosure is directed to a method including receiving EGM signal data for a cardiac episode detected by an implantable medical device (IMD), wherein the EGM signal data includes at least ventricular sensed events and atrial sensed events; determining, based on a probabilistic analysis, whether the EGM signal data indicates ventricular over-sensing (VOS), wherein a determination that the EGM signal data indicates VOS comprises classifying the cardiac episode as inappropriately shocked; determining, in response to a determination that the EGM signal data does not indicate VOS, whether the EGM signal data indicates an atrial sensing issue, the atrial sensing issue including one of atrial over-sensing or atrial under-sensing, wherein: in response to a determination of the atrial sensing issue, the method further comprises determining whether the atrial sensing issues are repairable; in response to a determination that the atrial sensing issues are repairable, the method further comprises repairing the sensing issues and classifying the cardiac episode based on a set of classification rules that consider both the ventricular and atrial sensed events; in response to a determination that the atrial sensing issues are not repairable, the method further comprises classifying the cardiac episode based on at least one classification rule that considers the ventricular sensed events but not the atrial sensed events; and the classification of the cardiac episode comprises one of ventricular tachycardia/ventricular fibrillation, inappropriately shocked, or indeterminate.

In another example, the disclosure is directed to system including a communication module configured to receive EGM signal data for a cardiac episode detected by an implantable medical device (IMD), wherein the EGM signal data includes at least ventricular sensed events and atrial sensed events. The system also includes a processor configured to: determine, based on a probabilistic analysis, whether the EGM signal data indicates ventricular over-sensing (VOS), wherein the determination is based at least in part on a probabilistic determination of whether the EGM signal data indicates T-wave over-sensing (TWOS) and wherein a determination of VOS comprises classifying the cardiac episode as inappropriately shocked; determine, in response to a determination of no VOS, whether the EGM signal data indicates an atrial sensing issue, the atrial sensing issue including one of atrial over-sensing or atrial under-sensing, wherein in response to a determination of the atrial sensing issue, determine whether the atrial sensing issues are repairable, in response to a determination that the atrial sensing issues are repairable, repair the sensing issues and classifying the cardiac episode based on a set of classification rules that consider both the ventricular and atrial sensed events; in response to a determination that the atrial sensing issues are not repairable, classify the cardiac episode based on at least one classification rule that considers the ventricular sensed events but not the atrial sensed events; and wherein the classification comprises ventricular tachycardia/ventricular fibrillation, inappropriately shocked, or indeterminate.

In another example, the disclosure is directed to a computer-readable medium containing instructions. The instructions cause a programmable processor to receive EGM signal data for a cardiac episode detected by an implantable medical device (IMD), wherein the EGM signal data includes at least ventricular sensed events and atrial sensed events; determine, based on a probabilistic analysis, whether the EGM signal data indicates ventricular over-sensing (VOS), wherein the determination is based at least in part on a probabilistic determination of whether the EGM signal data indicates T-wave over-sensing (TWOS) and wherein a determination of VOS comprises classifying the cardiac episode as inappropriately shocked; determine, in response to a determination of no VOS, whether the EGM signal data indicates an atrial sensing issue, the atrial sensing issue including one of atrial over-sensing or atrial under-sensing, wherein in response to a determination of the atrial sensing issue, determine whether the atrial sensing issues are repairable, in response to a determination that the atrial sensing issues are repairable, repair the sensing issues and classifying the cardiac episode based on a set of classification rules that consider both the ventricular and atrial sensed events; in response to a determination that the atrial sensing issues are not repairable, classify the cardiac episode based on at least one classification rule that considers the ventricular sensed events but not the atrial sensed events; and wherein the classification comprises ventricular tachycardia/ventricular fibrillation, inappropriately shocked, or indeterminate.

In another example, the disclosure is directed to a system including means for receiving EGM signal data for a cardiac episode detected by an implantable medical device (IMD), wherein the EGM signal data includes at least ventricular sensed events and atrial sensed events; means for determining, based on a probabilistic analysis, whether the EGM signal data indicates ventricular over-sensing (VOS), wherein a determination that the EGM signal data indicates VOS comprises classifying the cardiac episode as inappropriately shocked; means for determining, in response to a determination that the EGM signal data does not indicate VOS, whether the EGM signal data indicates an atrial sensing issue, the atrial sensing issue including one of atrial over-sensing or atrial under-sensing, wherein: in response to a determination of the atrial sensing issue, the method further comprises determining whether the atrial sensing issues are repairable; in response to a determination that the atrial sensing issues are repairable, the method further comprises repairing the sensing issues and classifying the cardiac episode based on a set of classification rules that consider both the ventricular and atrial sensed events; in response to a determination that the atrial sensing issues are not repairable, the method further comprises classifying the cardiac episode based on at least one classification rule that considers the ventricular sensed events but not the atrial sensed events; and the classification of the cardiac episode comprises one of ventricular tachycardia/ventricular fibrillation, inappropriately shocked, or indeterminate.

The details of one or more examples consistent with the present disclosure are set forth in the accompanying drawings and the description below. Other features, objects, and advantages of the disclosure will be apparent from the description and drawings, and from the claims.

DETAILED DESCRIPTION

Figure 1:
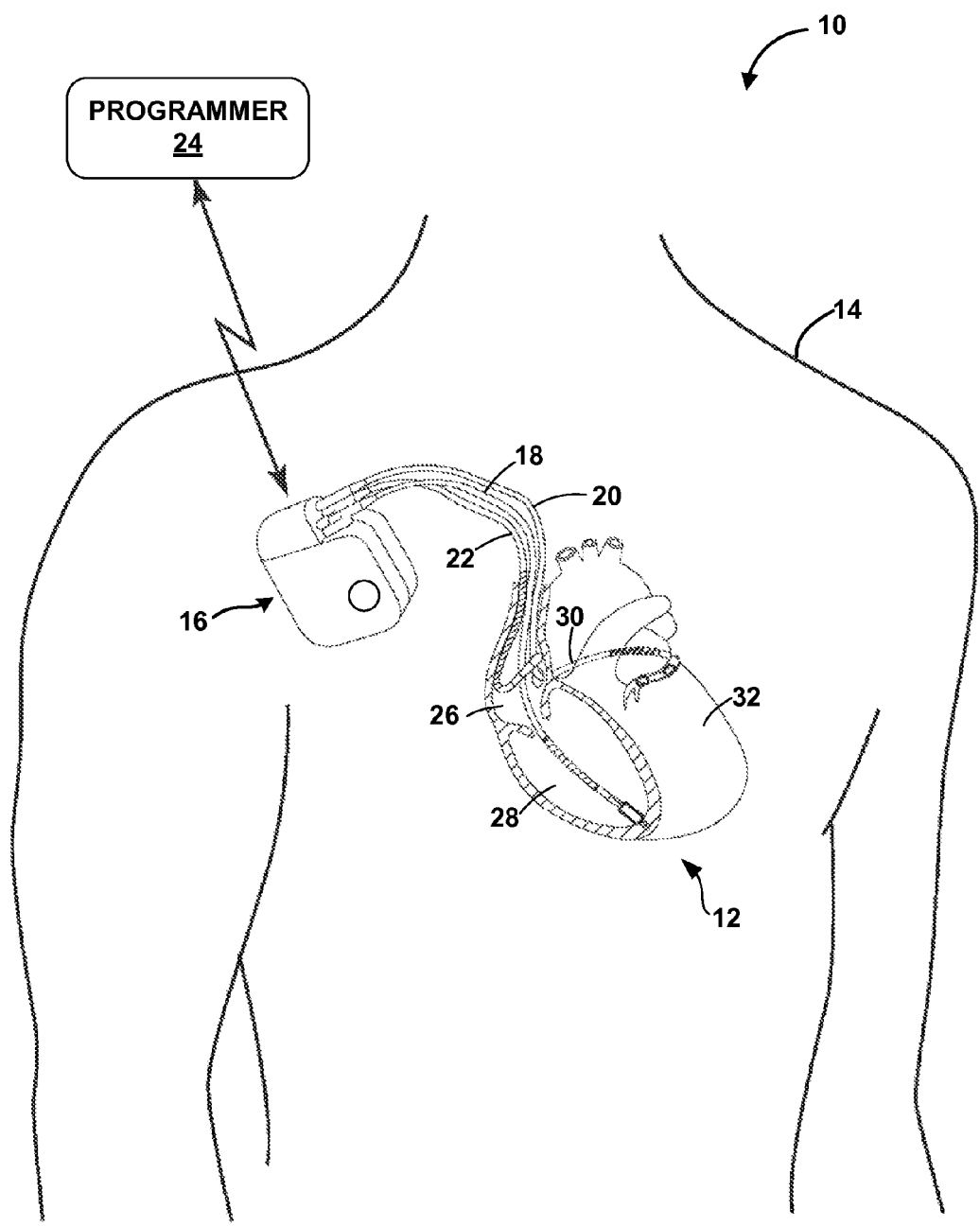
FIG. 1 is a conceptual diagram illustrating an example system for monitoring and treating cardiac events and analyzing the effectiveness of an IMD.

This disclosure describes techniques for classifying cardiac episodes. In particular, the disclosure describes techniques for identifying characteristics in an EGM signal that may lead to an IMD misclassifying an episode. In some examples, the techniques are implemented by either an IMD or by an external device to evaluate a prior classification of an episode by the IMD.

In general, an IMD transmits electrogram (EGM) signal data or other data associated with a cardiac episode diagnosed by the IMD to an external computing device. In some examples the data is transmitted after the episode is over. In some examples, data for one or more episodes is transmitted at predetermined intervals. The data stored by an IMD for a cardiac episode diagnosed by the IMD may include the diagnosis made by the IMD and data leading up to diagnosis of the particular cardiac episode. In some examples, IMD may include episodes resulting in either anti-tachycardia pacing or a shock in response to a diagnosis of either ventricular tachycardia or ventricular fibrillation. It is also possible that the IMD may have misdiagnosed a supraventricular tachycardia (SVT), such as sinus tachycardia or an atrial arrhythmia, or noise as a treatable, e.g., shockable, episode.

In some examples, an external computing device analyzes the EGM signal that was previously used by the IMD to classify an episode, and generates its own classification of the episode based on the EGM signal. In some examples, the external device determines whether the classification of the episode by the IMD was correct by comparing its classification of the episode to that of the IMD. The techniques described below may reduce the number of episodes that the external device is unable to classify with a reasonable degree of confidence.

In some examples, a post-processing classification algorithm may reduce the number of EGM episodes that are unable to be classified confidently employing a probabilistic determination of VOS. The use of a probabilistic determination of VOS allows for classification of episodes that may have previously been categorized as indeterminate. As part of the probabilistic determination of VOS algorithm, a post-processing classification algorithm may also use a probabilistic determination of TWOS. This again increases the number of episodes properly classified as having sensing issues and decreases the number of episodes categorized as indeterminate.

When using either probabilistic detection of VOS or probabilistic detection of TWOS, an algorithm may look at a number of factors, none of which may be dispositive. However, the algorithm assigns various weights to each factor for or against the presence of the particular over-sensing issue. After all the factors have been studied, the evidence for and against a particular sensing issue is summed and compared. In general, if there is more evidence for oversensing, by weight and not necessarily the number of factors themselves, then the algorithm determines that the episode includes oversensing which interfered with the proper classification of the rhythm by the implantable medical device. In some examples, the presence of oversensing may result in changes to one or more parameters used by the IMD to diagnosis arrhythmias.

In some examples, a post-processing classification algorithm may reduce the number of EGM episodes that are unable to be classified confidently by determining if the EGM signal indicates the presence of atrial sensing issues. The algorithm may determine if the sensing issues are correctable. If the sensing issues are not correctable, classification rules that do not rely on atrial sensing may be used to classify the episode.

In some examples, a post-processing classification algorithm may reduce the number of EGM episodes that are unable to be classified confidently by determining if the EGM signal indicates the presence of atrial fibrillation (AF). The algorithm may look at a number of characteristics of the EGM signal that may be evidence of AF. Based on the all the evidence a determination is made as to whether or not it is likely the episode is AF.

In some examples, a post-processing classification algorithm may reduce the number of EGM episodes that are unable to be classified confidently by determining whether an episode was properly diagnosed in the presence of pacing. This algorithm may allow for an increase in the types of episodes that may be classified during post-processing. For examples, episodes during cardiovascular resynchronization therapy (CRT) may be classified, despite the presence of pacing pulses.

Overall, the various algorithms discussed in this disclosure have been found to reduce the number of indeterminate classifications by 92% while also reducing the number of misclassifications by 24%. In addition, the algorithms improve tolerance of atrial sensing issues by 64% while increasing correct classification of episodes with atrial sensing issue by 50 to 62%.

FIG. 1 is a conceptual diagram illustrating an example system 10 for monitoring and treating cardiac episodes and analyzing the effectiveness of an implantable medical device (IMD) 16. As illustrated in FIG. 1, a system for monitoring and treating cardiac episodes and providing a summary of the episodes to an external device for review includes an IMD 16, such as an implantable cardiac pacemaker, implantable cardioverter/defibrillator (ICD), or pacemaker/cardioverter/defibrillator, for example. IMD 16 is connected to leads 18, 20 and 22 and is communicatively coupled to a programmer 24. IMD 16 senses electrical signal attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16, the therapy may be pacing, cardioversion and/or defibrillation pulses. IMD 16 may monitor EGM signals collected by electrodes on leads 18, 20 or 22, and based on the EGM signal diagnosis and treat cardiac episodes. Programmer 24 may receive and summarize the EGM signal based diagnosis and treatment of cardiac episodes provided by IMD 16. The system for summarizing and displaying information regarding diagnosis and treatment may also be used with other medical devices, such as a cardiomyostimulator, a drug delivery system, cardiac and other physiological monitors.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, programmer 24 takes the form of a handheld computing device, computer workstation or networked computing device that includes a user interface for presenting information to and receiving input from a user. A user, such as a physician, technician, surgeon, electro-physiologist, or other clinician, may interact with programmer 24 to retrieve physiological or diagnostic information from IMD 16. Programmer 24 may provide to the user a summary of physiological and diagnostic information for patient 12 over a period of time. A user may also interact with programmer 24 to program IMD 16, e.g., select values for operational parameters of the IMD. Programmer 24 may include a processor configured to evaluate EGM signals transmitted from IMD 16 to programmer 24. In some examples, programmer 24 may evaluate a prior classification of an episode by IMD 16.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In some examples, programmer 24 may be located remotely from IMD 16, and communicate with IMD 16 via a network. Programmer 24 may also communicate with one or more other external devices using a number of known communication techniques, both wired and wireless.

In some examples, data acquired by IMD 16 can be monitored by an external system, such as the programmer 24. Programmer 24 may analyze characteristics of EGM signals data corresponding to cardiac episodes recognized by IMD 16. Arrhythmia analysis of cardiac episodes according to an example of the present disclosure may take place in the programmer 24 once the required data is transmitted from IMD 16 to the programmer 24. In some examples, programmer 24 may transmit the required data to another external device, not shown in FIG. 1, for analysis.

Figure 2:
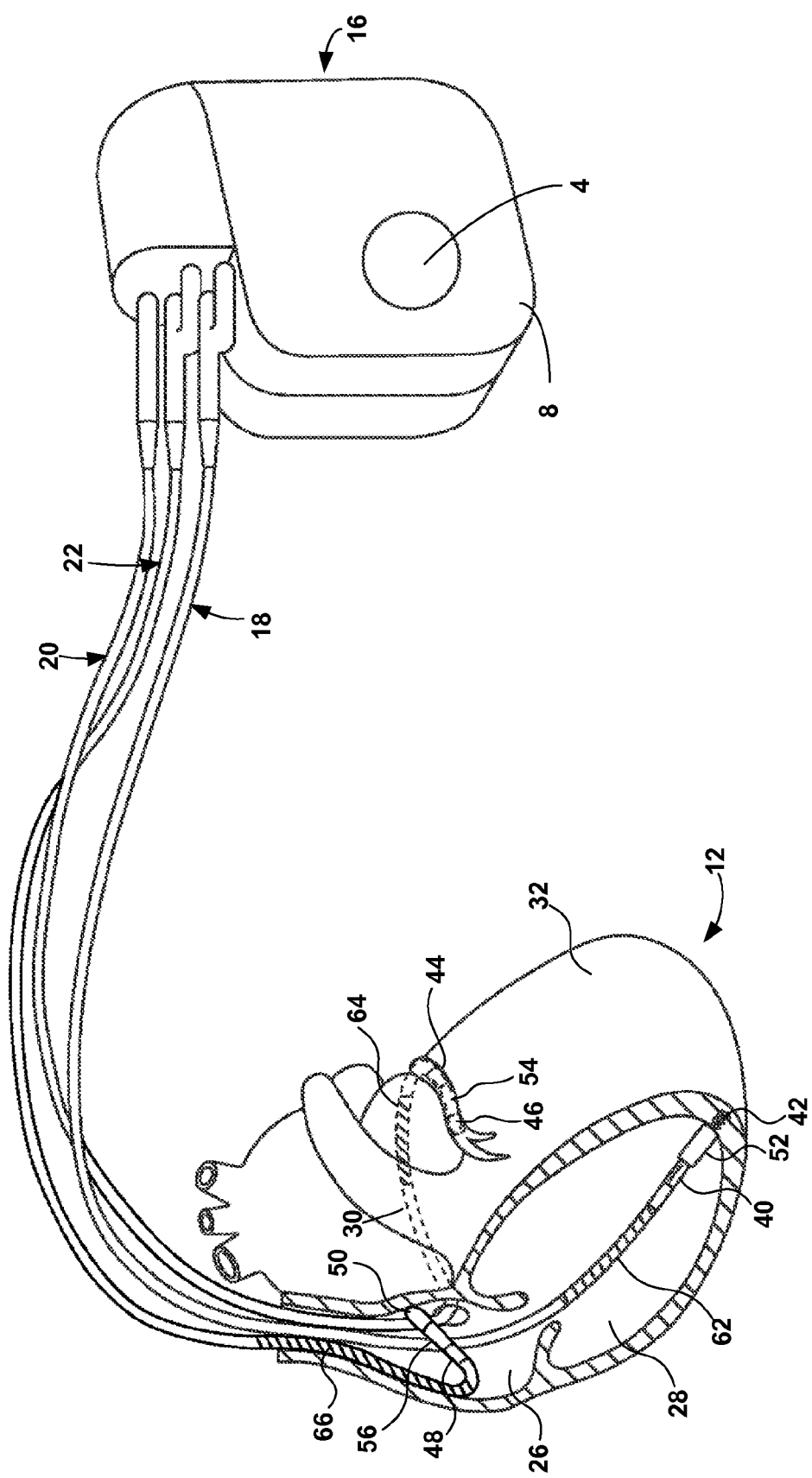
FIG. 2 is a conceptual diagram illustrating the IMD and leads of the system of FIG. 1 in greater detail.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative embodiments, not shown in FIG. 2, one or more of leads 18, 20 and 22, e.g., left-ventricular lead 20, may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes 40, 42, 44, 46, 48, 50, 62, 64 and 66 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

Housing 8 encloses a signal generator that generates therapeutic stimulation, such as cardiac pacing, cardioversion and defibrillation pulses, as well as a sensing module for sensing electrical signals attendant to the depolarization and repolarization of heart 12. Housing 8 may also enclose a memory for storing the sensed electrical signals. Housing 8 may also enclose a telemetry module for communication between IMD 16 and programmer 24.

IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or subcutaneous leads not positioned within the heart.

Figure 3:
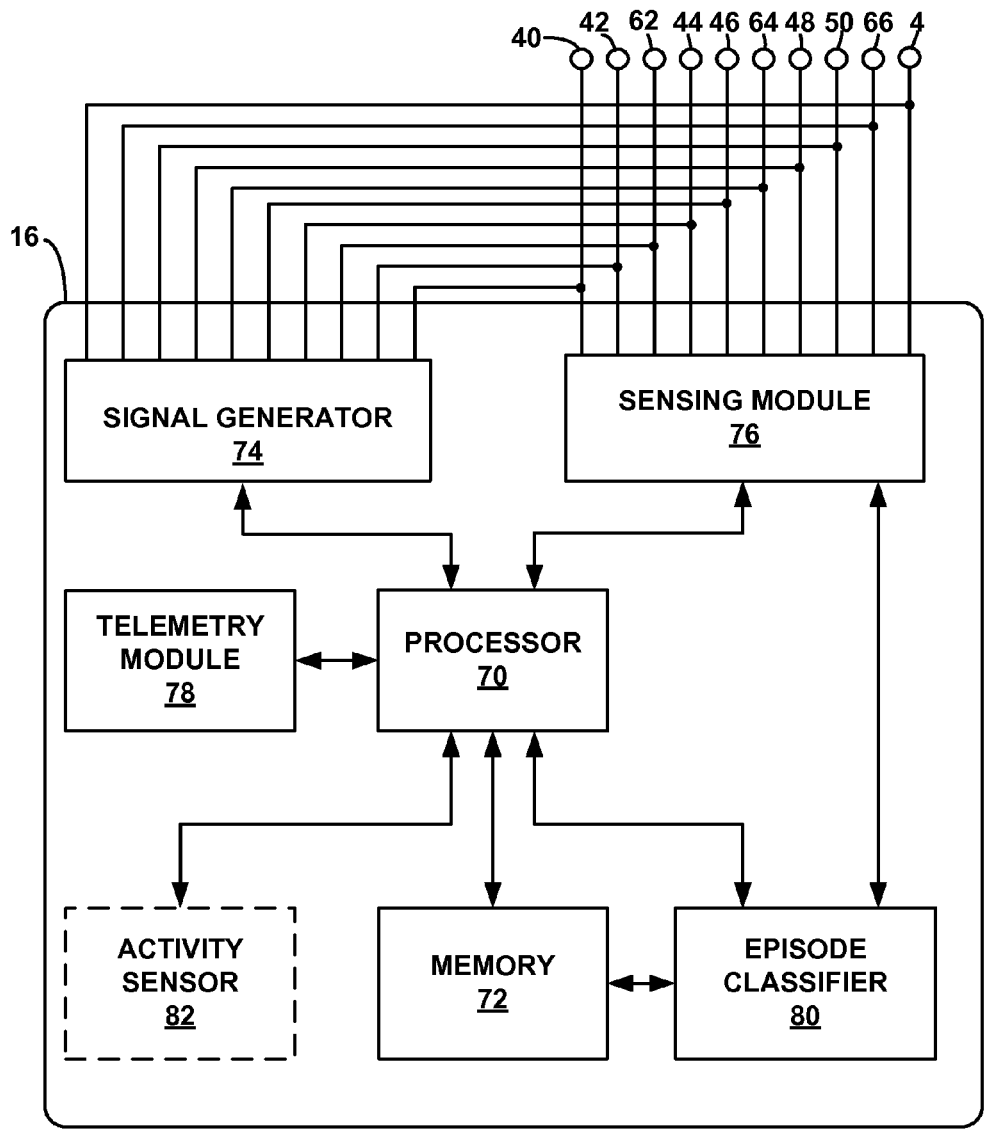
FIG. 3 is a block diagram illustrating an example IMD that monitors cardiac electrogram (EGM) signals and classifies abnormal signals before providing a therapeutic response.

FIG. 3 is a block diagram illustrating an example IMD 16 that monitors EGM signals and classifies abnormal signals before providing a therapeutic response. In the illustrated example, IMD 16 includes a processor 70, memory 72, signal generator 74, sensing module 76, telemetry module 78, episode classifier 80, and activity sensor 82. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs or parameters. Processor 70 may modify the electrical pulses delivered by signal generator 74 based on a diagnosis or classification of an EGM signal by episode classifier 80.

Signal generator 74 is configured to generate and deliver electrical stimulation therapy to patient 14. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, within housing 8. For example, signal generator 74 may deliver pacing, defibrillation or cardioversion pulses to heart 12 via at least two of electrodes 4, 40, 42, 44, 46, 48, 50, 62, 64 and 66. In some examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70. One or more other detection channels may provide the signals to an analog-to-digital converter, for conversion into a digital signal for processing or analysis by processor 70 or episode classifier 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76 or processor 70. Processor 70 may analyze the digitized version of signals from the wide band channel. Processor 70 may employ digital signal analysis techniques to characterize the digitized signals from the wide band channel to, for example, detect and classify the patient's heart rhythm.

Episode classifier 80 may detect and classify the patient's heart rhythm based on the cardiac electrical signals sensed by sensing module 76 employing any of the numerous signal processing methodologies known in the art. For example, episode classifier 80 may maintain escape interval counters that may be reset upon sensing of R-waves by sensing module 76. The value of the count present in the escape interval counters when reset by sensed depolarizations may be used by episode classifier 80 to measure the durations of R-R intervals, which are measurements that may be stored in memory 72. Episode classifier 80 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by episode classifier 80 to determine whether the patient's heart 12 is presently exhibiting atrial or ventricular tachyarrhythmia.

In some examples, episode classifier 80 may determine that tachyarrhythmia has occurred by identification of shortened R-R interval lengths. Generally, episode classifier 80 detects tachycardia when the interval length falls below 360 milliseconds (ms) and fibrillation when the interval length falls below 320 ms. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, episode classifier 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by episode classifier 80 in some examples. For example, EGM morphology may be considered in addition to or instead of interval length for detecting tachyarrhythmias.

Generally, episode classifier 80 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase. Again, in some cases, episode classifier 80 may mistakenly classify the patient's heart rhythm as a treatable tachyarrhythmia, e.g., as a result of a noisy EGM or over-sensing. In order to learn more about when IMD 16 is misclassifying patient's heart rhythms as shockable episodes, episode classifier 80 may send a portion of an EGM signal that resulted in a classification of a treatable tachyarrhythmia.

In some examples, episode classifier 80 sends a portion of the EGM signal to memory 72 to be saved on an ongoing basis. When a tachyarrhythmia is not detected the EGM signal may be written over after a period of time. In response to a tachyarrhythmia being detected, episode classifier 80 may direct memory 72 to store on a long term basis a time period or portion of the EGM signal leading up to the diagnosis of the tachyarrhythmia, along with the specific diagnosis, e.g., ventricular tachycardia, ventricular fibrillation or supraventricular tachycardia. In some examples, a diagnosis may not result in stimulation being provided by IMD 16. The corresponding EGM signal may be categorized as non-sustained ventricular tachycardia atrial tachycardia or atrial fibrillation or a monitored ventricular tachycardia episode.

Episode classifier 80 or processor 70 may implement one or more algorithms to determine if VOS, TWOS, or atrial sensing issues are present. The presence of one or more of VOS, TWOS, or atrial sensing may affect the episode classification by episode classifier 80, as well as possible treatment selection by processor 70.

Although processor 70 and episode classifier 80 are illustrated as separate modules in FIG. 3, processor 70 and episode classifier 80 may be incorporated in a single processing unit. Episode classifier 80 may be a component of, or a software or firmware module executed by, processor 70.

Activity sensor 82 may be optionally included in some examples of IMD 16. Activity sensor 82 may include one or more accelerometers. Activity sensor 82 may additionally or alternatively include other sensors such as a heart sounds sensor, a pressure sensor, or an $O_2$ saturation sensor. In some examples, activity sensor 82 may detect respiration via one or more electrodes. Information obtained from activity sensor 82 may be used to determine activity level, posture, blood oxygen level or respiratory rate, for example, leading up to, or at the time of, the abnormal heart rhythm. In some examples, this information may be used by IMD 16 to aid in the classification of an abnormal heart rhythm.

Activity sensor 82 may, for example, take the form of one or more accelerometers, or any other sensor known in the art for detecting activity, e.g., body movements or footfalls, or posture. In some examples, activity sensor 82 may comprise a three-axis accelerometer. Processor 70 may determine an activity level count at regular intervals based on the signal(s) from activity sensor 82. In some examples, processor 70 may determine a running average activity count based on the information provided by activity sensor 82. For example, the activity count may be calculated over a 1 second interval and the processor 70 may update the activity level count at a 1 second interval. A method of determining activity count from an accelerometer sensor is described in U.S. Pat. No. 6,449,508, to Sheldon et al, entitled, "ACCELEROMETER COUNT CALCULATION FOR ACTIVITY SIGNAL FOR AN IMPLANTABLE MEDICAL DEVICE," issued Sep. 10, 2002, and incorporated herein by reference in its entirety.

Activity sensor 82 may be located outside of the housing 8 of IMD 16. Activity sensor 82 may be located on a lead that is coupled to IMD 16 or may be implemented in a remote sensor that wirelessly communicates with IMD 16 via telemetry module 78. In any case, activity sensor 82 is electrically or wirelessly coupled to circuitry contained within housing 8 of IMD 16.

Telemetry module 78 includes any suitable hardware, firmware, software or any combination thereof for communicating with another device, such as programmer 24 (FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., ECG or EGM signals, produced by sensing module 76 and/or signals selected by episode classifier 80 to programmer 24. Processor 70 may also generate and store marker codes indicative of different cardiac or other physiological events detected by sensing module 76 or episode classifier 80, and transmit the marker codes to programmer 24. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 70 may transmit to programmer 24 via telemetry module 78 may also include an indication of a change in disease state of the heart, an indication of a change in heart response to the therapy provided or an indication that the heart continues to response in the same (or similar) manner to the therapy provided, the indications based on heart sounds and/or EGM signals. Such information may be included as part of a marker channel with an EGM.

Figure 4:
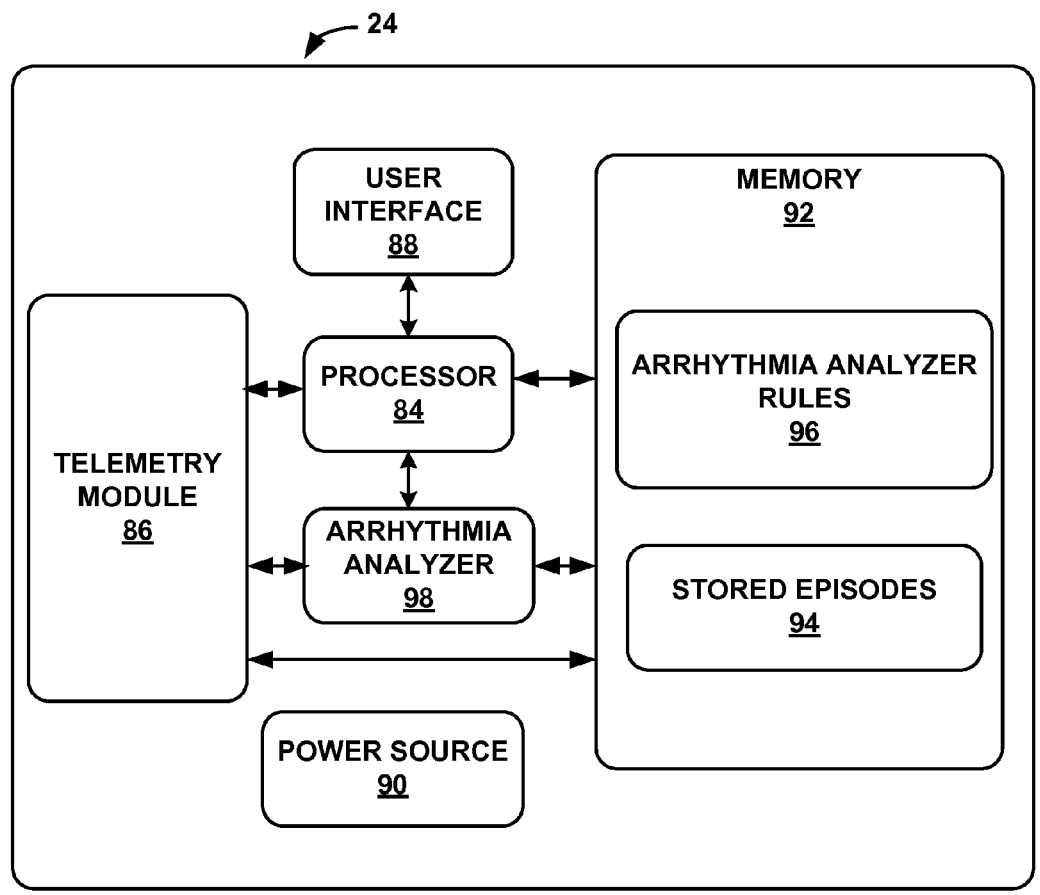
FIG. 4 is a block diagram illustrating an example external programmer shown in FIG. 1.

FIG. 4 is a block diagram illustrating an example external programmer 24. As illustrated in FIG. 4, programmer 24 may include a processor 84, a memory 92, a telemetry module 86, a user interface 88, a power source 90 and an arrhythmia analyzer 98. Processor 84 stores and retrieves information and instructions to and from memory 92. Processor 84 may include a microprocessor, a microcontroller, a DSP, an ASIC, an FPGA, or other equivalent discrete or integrated logic circuitry. Accordingly, processor 84 may include any suitable structure, whether in hardware, software, firmware or any combination thereof, to perform the functions ascribed herein to processor 84.

Figure 5:
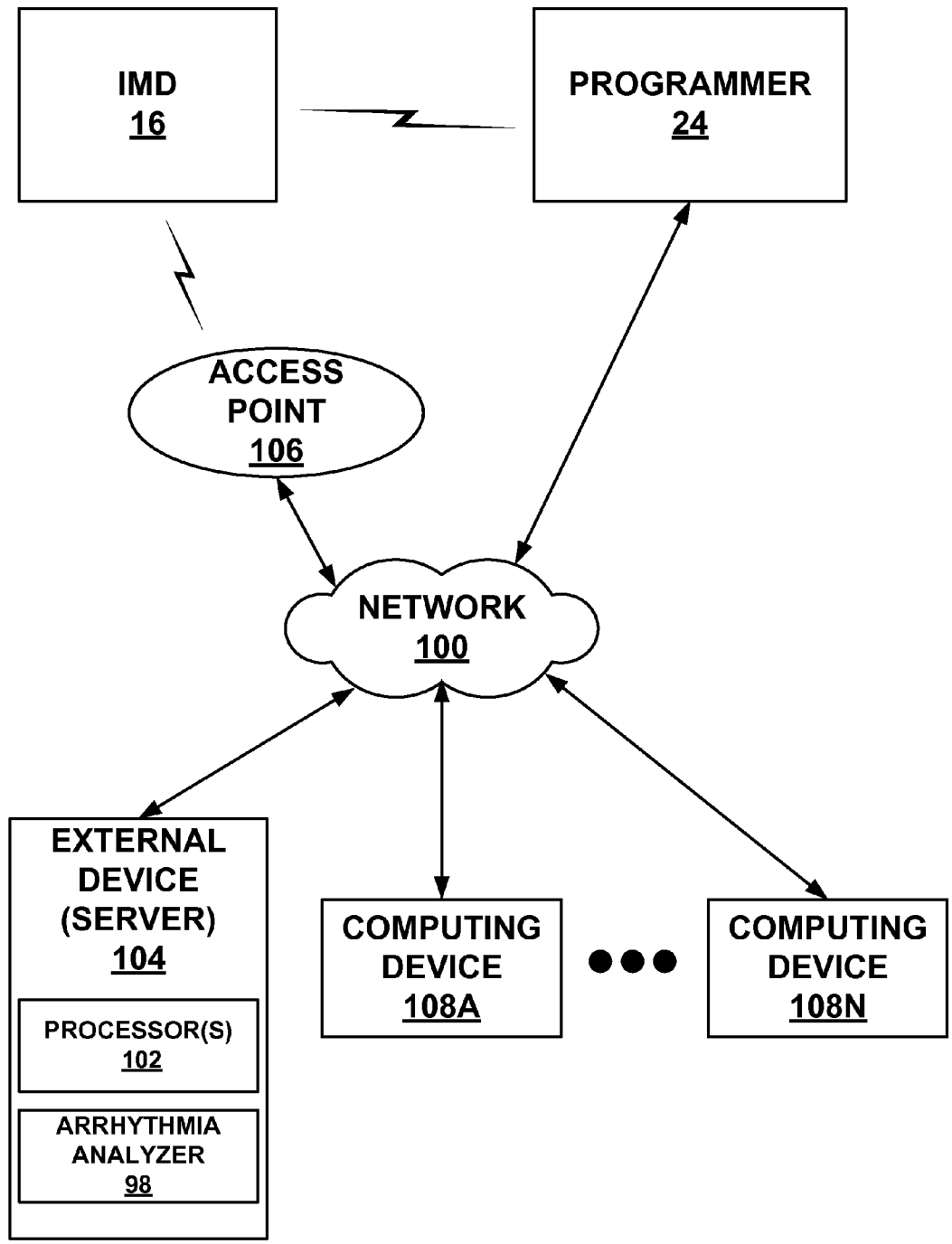
FIG. 5 is a block diagram illustrating an example system that includes an external device, such as a server, and one or more computing devices that are coupled to the IMD and programmer shown in FIG. 1 via a network.

Telemetry module 86 receives EGM signal data from IMD 16. In some examples, the EGM Signal data is transmitted from IMD via access point 106 and network 100, as shown in FIG. 5. The EGM signal data may be transmitted to telemetry module 86 in response to IMD 16 diagnosing an arrhythmia and responding with electrical stimulation. In some examples, portions of EGM signal data are stored in memory 72 of IMD 16 until a predetermined event occurs. After the event has occurred, the data is transmitted via telemetry module 78 of IMD 16 to telemetry module 86 of programmer 24. For example, every three months IMD 16 may transmit EGM signal data selected by episode classifier 80 and stored in memory 72.

A user, such as a clinician or patient, may interact with programmer 24 through user interface 88. Accordingly, in some examples programmer 24 may comprise a patient programmer or a clinician programmer. The techniques of this disclosure are directed post-processing of EGM signals collected by IMD 16 and used by IMD 16 to diagnosis treatable arrhythmias. The post-processing is used to determine whether IMD 16 correctly diagnosed the detected arrhythmia. Therefore, many of the functions ascribed to programmer 24, and in particular processor 84, may be performed by any one or more external devices, such as any one or more of programmer 24, external device 104 (FIG. 5) or another computing device, e.g., computing device 108 (FIG. 5). In some examples programmer 24 may function as a user interface while processing occurs on external device 104. When programmer 24 is configured as a patient programmer, in some examples, the patient programmer is not necessarily configured to perform the post-processing or provide information regarding the accuracy of diagnosis to the patient. In some examples, when programmer 24 is configured as a clinician programmer, processor 84 may be configured to perform the post-processing using arrhythmia analyzer 98 and arrhythmia analyzer rules 96.

Although processor 84 and arrhythmia analyzer 98 are illustrated as separate modules in FIG. 4, processor 84 and arrhythmia analyzer 98 may be incorporated in a single processing unit. Arrhythmia analyzer 98 may be a component of or a module executed by processor 84.

User interface 88 includes a display (not shown), such as a LCD or LED display or other type of screen, to present information related to the therapy, such as information related to current stimulation parameters and electrode combinations and when configured to allow a physician to review EGM information transmitted from IMD 16, including information regarding cardiac episode classification by episode classifier 80 of IMD 16. In some examples, user interface 88 may display information regarding the results of arrhythmia analyzer 98. In addition, user interface 88 may include an input mechanism to receive input from the user. The input mechanisms may include, for example, buttons, a keypad (e.g., an alphanumeric keypad), a peripheral pointing device, or another input mechanism that allows the user to navigate through user interfaces presented by processor 84 of programmer 24 and provide input. The input may include, for example, selection of one or more cardiac episodes transmitted from IMD 16 for arrhythmia analysis by arrhythmia analyzer 98.

If programmer 24 includes buttons and a keypad, the buttons may be dedicated to performing a certain function, e.g., a power button, or the buttons and the keypad may be soft keys that change in function depending upon the section of the user interface currently viewed by the user. Alternatively, the display (not shown) of programmer 24 may be a touch screen that allows the user to provide input directly to the user interface shown on the display. The user may use a stylus or a finger to provide input to the display. In other examples, user interface 88 also includes audio circuitry for providing audible instructions or sounds to patient 14 and/or receiving voice commands from patient 14, which may be useful if patient 14 has limited motor functions.

Patient 14, a clinician, or another user may also interact with programmer 24 to manually select values for operational parameters of IMD 16, and thereby control the cardiac sensing and stimulation functionality of the IMD. In some examples, modification to operational parameters may be made in response to the results of arrhythmia analysis by arrhythmia analyzer 98. For example, programmer 24 may modify detection algorithms used by episode classifier 80 in response to the results of arrhythmia analysis of one more episodes by arrhythmia analyzer 98.

Processor 84 receives a segment of EGM signal data representing a cardiac episode resulting in a diagnosis of an arrhythmia followed by electrical stimulation based on the diagnosis. The episode may be received from telemetry module 86 or from memory 92. The episodes received from IMD 16 may be stored in stored episodes 94 until retrieved by processor 84 or arrhythmia analyzer 98 for display or classification. Arrhythmia analyzer 98 may use arrhythmia analyzer rules stored in arrhythmia analyzer rules 96 to analyze a cardiac episode. Processor 84 may select stored episodes 94 for retrospective analysis based on whether the diagnosis of the cardiac episode by episode classifier 80 of IMD 16 and the classification by arrhythmia analyzer 98 conflict.

As shown in FIG. 4, memory 92 includes stored episodes 94, and arrhythmia analyzer rules 96 in separate memories within memory 92 or separate areas within memory 92. Memory 92 may also include instructions for operating user interface 88, telemetry module 86, and for managing power source 90. Memory 92 may include any volatile or nonvolatile memory such as RAM, ROM, EEPROM or flash memory. Memory 92 may also include a removable memory portion that may be used to provide memory updates or increases in memory capacities. A removable memory may also allow sensitive patient data to be removed before programmer 24 is used by, or for, a different patient.

Stored episodes 94 stores EGM signal data received from IMD 16 via telemetry module 86. In some examples, the EGM signal data is separated into episodes, and each episode is saved along with a diagnosis made by IMD 16 based on the EGM signal data in the episode. IMD 16 may transmit EGM signal data at predetermined time intervals, for example every three months. The EGM signals are received by telemetry module 86 and stored in stored episodes 94. In some examples, processor 84 retrieves episodes stored in stored episodes 94 one at a time and confirms or rejects the diagnosis of IMD 16 using arrhythmia analyzer rules stored in episode classification rule 96.

Arrhythmia analyzer rules 96 stores one or more classification algorithms or sets of classification rules used by arrhythmia analyzer 98 to perform retrospective arrhythmia analysis to classify cardiac episodes transmitted by IMD 16 to programmer 24. In some examples, the arrhythmia analyzer rules classify each episode as supraventricular tachycardia (SVT), ventricular tachycardia or ventricular fibrillation (VT/VF), or unknown. The arrhythmia analyzer rules may also determine if any misclassifications are based on VOS or TWOS. The classification rules may, in some examples, provide comments regarding reason for a particular classification, including, for example, whether VOS or TWOS was present. In some examples, the classifications are compared to the diagnosis generated by IMD 16 prior to delivery therapy.

Arrhythmia analyzer 98 may apply arrhythmia analyzer rules stored in arrhythmia analyzer rules 96 to a cardiac episode. Episodes received from IMD 16 may be stored in stored episodes 94 until retrieved by arrhythmia analyzer 98 for classification. In addition to a classification, arrhythmia analyzer 98 may also determine whether the EGM signal of the cardiac episode indicates the presence of one or sensing problems such as VOS and TWOS.

FIG. 5 is a block diagram illustrating an example system that includes an external device 104, such as a server, and one or more computing devices 108A-108N that are coupled to the IMD 16 and programmer 24 shown in FIG. 1 via a network 100. Network 100 may be generally used to transmit diagnostic information (e.g., a diagnosis made by IMD 16 of an abnormal cardiac rhythm based on an EGM signal obtained by the IMD) from an IMD 16 to a remote external computing device. In some examples, EGM signals may be transmitted to an external device for display to a user. In some examples, the EGM signal is subjected to retrospective analysis by the external device resulting in a post-processing classification of the cardiac episode.

In some examples, the information transmitted by IMD 16 may allow a clinician or other healthcare professional to monitor patient 14 remotely. In some examples, IMD 16 may use a telemetry module 78 to communicate with programmer 24 via a first wireless connection, and to communicate with access point 106 via a second wireless connection, e.g., at different times. In the example of FIG. 5, access point 106, programmer 24, server 104 and computing devices 108A-108N are interconnected, and able to communicate with each other through network 100. In some cases, one or more of access point 106, programmer 24, server 104 and computing devices 108A-108N may be coupled to network 100 via one or more wireless connections. IMD 16, programmer 24, server 104, and computing devices 108A-108N may each comprise one or more processors, such as one or more microprocessors, DSPs, ASICs, FPGAs, programmable logic circuitry, or the like, that may perform various functions and operations, such as those described herein.

Access point 106 may comprise a device that connects to network 100 via any of a variety of connections, such as telephone dial-up, digital subscriber line (DSL), or cable modem connections. In other examples, access point 106 may be coupled to network 100 through different forms of connections, including wired or wireless connections. In some examples, access point 106 may be co-located with patient 14 and may comprise one or more programming units and/or computing devices (e.g., one or more monitoring units) that may perform various functions and operations described herein. For example, access point 106 may include a home-monitoring unit that is co-located with patient 14 and that may monitor the activity of IMD 16. In some examples, server 104 or computing devices 108 may control or perform any of the various functions or operations described herein, e.g., determine, based on EGM signal data, whether IMD 16 properly classified various cardiac episodes, and display a summary of the EGM signal data transmitted by IMD 16.

In some cases, server 104 may be configured to provide a secure storage site for archival of diagnostic information (e.g., occurrence of a diagnosis and shock by IMD 16 and attendant circumstances such as the EGM signal leading up to the diagnosis) that has been collected and generated from IMD 16 and/or programmer 24. Network 100 may comprise a local area network, wide area network, or global network, such as the Internet. In some cases, programmer 24 or server 104 may assemble EGM signal and diagnosis information in web pages or other documents for viewing by trained professionals, such as clinicians, via viewing terminals associated with computing devices 108. The system of FIG. 5 may be implemented, in some aspects, with general network technology and functionality similar to that provide by the Medtronic CareLink® Network developed by Medtronic, Inc., of Minneapolis, Minn.

In the example of FIG. 5, external server 104 may receive EGM signal data from IMD 16 via network 100. Based on the EGM signal data received, processor(s) 102 may preform one or more of the functions described with herein with respect to processor 84 and/or arrhythmia analyzer 98 of programmer 24, e.g., processor(s) 102 of server 104 may implement or comprise an arrhythmia analyzer 98 that analyzes EGM signals from IMD 16 according to arrhythmia analyzer rules 96. Computing device 108 may also include a processor that performs one or more of the functions described herein with respect to processor 84 and/or arrhythmia analyzer 98 of programmer 24. In various examples, arrhythmia analysis may be carried out by any of the programmer 24, external server 104 or computing device 108.

Figure 6:
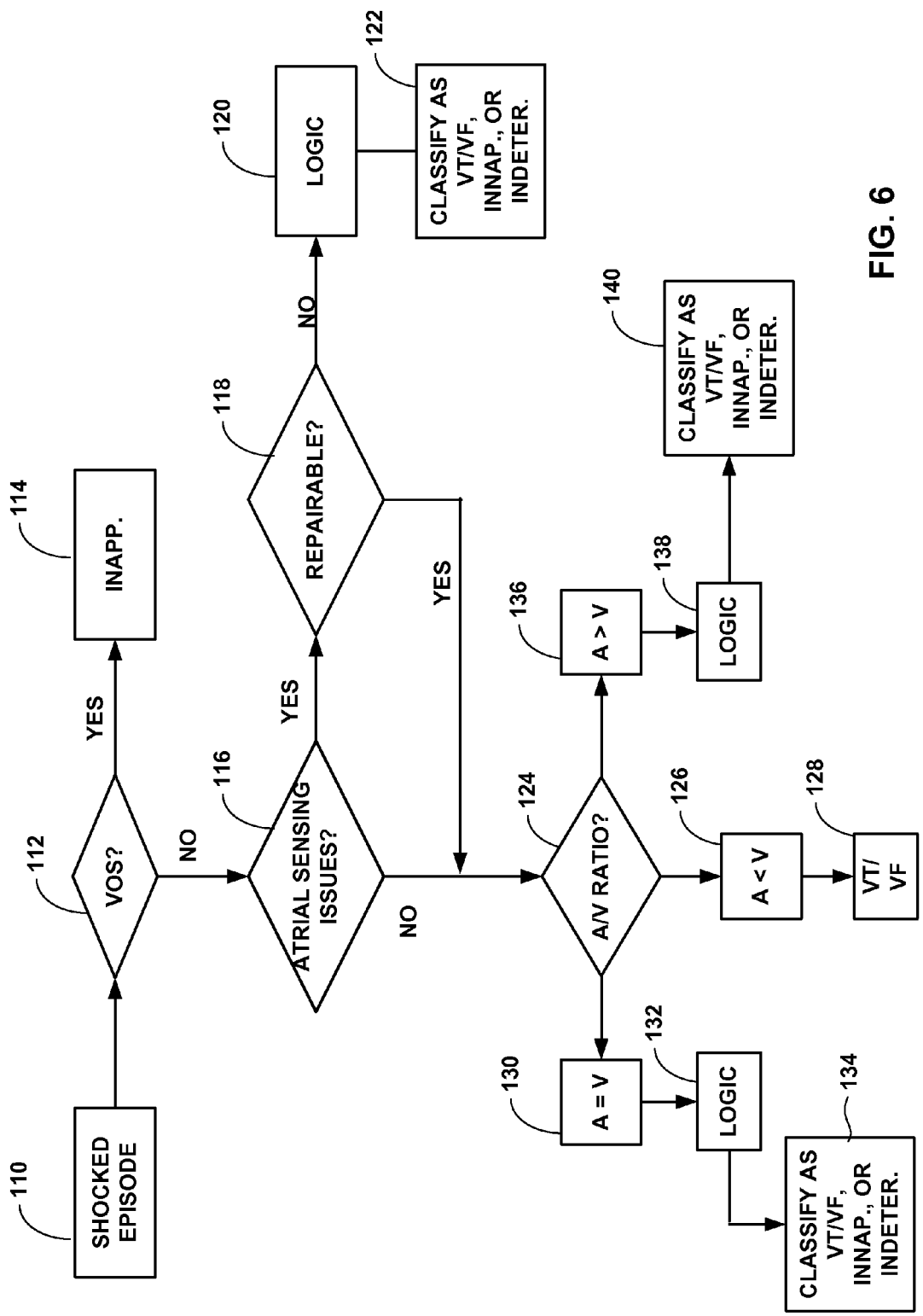
FIG. 6 is a flow diagram illustrating an example arrhythmia analysis sequence implemented by an arrhythmia analyzer.

FIG. 6 is a flow chart illustrating an example arrhythmia analysis sequence implemented by arrhythmia analyzer 98, which may be implemented in any one or more programmer 24, external server 104, computing device 108, any other computing device, or any combination thereof Arrhythmia analyzer 98 retrieves a shocked episode (110) from stored episodes 94. The arrhythmia analyzer 98 determines whether the EGM signal of the episode indicates the presence of the VOS (112). As explained in more detail below with respect to FIG. 7, arrhythmia analyzer 98 makes a probabilistic determination of whether VOS is present based on a number of criteria. Each criteria is assigned a weight for or against the presence of VOS, and based on the net outcome of the evaluation, arrhythmia analyzer 98 determines whether it is likely VOS is present in the EGM signal for the cardiac episode. If arrhythmia analyzer 98 determines that VOS is present, the arrhythmia analyzer 98 classifies the cardiac episode as one with receiving an inappropriate shock (114).

If VOS is not present, then arrhythmia analyzer 98 determines whether the EGM signal for the cardiac episode indicates the presence of atrial sensing issues (116). Although FIG. 6 illustrates determining VOS as occurring prior to determining whether the cardiac episodes includes atrial sensing issues, in other examples, not illustrated, the atrial sensing issue determination may be made prior to a determination of the presence of VOS. If arrhythmia analyzer 98 determines the presence of atrial sensing issues, arrhythmia analyzer 98 then determines if the atrial sensing issues are repairable (118). If the atrial sensing issues are not repairable, arrhythmia analyzer 98 applies logic (120) that does not rely on good atrial sensing. Factors that may be used to classify a cardiac episode in the presence of atrial sensing issues include, for examples, RR interval regularity or rate, the presence of atrial fibrillation (AF) characteristics, the rhythm after pacing, the frequency of the V signal, and ventricular morphology rules. Based on the classification rules, arrhythmia analyzer 98 may classify the cardiac episode as VT/VF, inappropriate (or SVT), or indeterminate (122). These factors will be described in more detail below with respect to FIG. 10.

A classification of VT/VF indicates that the arrhythmia analyzer 98 agrees with the classification by episode classifier 80 of IMD 16, and the decision to shock based on the EGM signal associated with the cardiac episode. A classification of inappropriate indicates that the arrhythmia analyzer 98 classified the cardiac episode as SVT, and therefore the shock provided was inappropriate treatment for the cardiac episode. A classification of indeterminate indicates that arrhythmia analyzer 98 was unable to determine whether the cardiac episode was properly classified as VT/VF or not.

If no atrial sensing issues are present, arrhythmia analyzer 98 continues to perform episode classification using algorithms that rely on one or both of atrial sensed events and ventricular sensed events. If the atrial sensing issues are repairable, then arrhythmia analyzer 98 or processor 84 repair the atrial sensing issues within the cardiac episode. After the atrial sensing issues are repaired, arrhythmia analyzer 98 continues to perform episode classification using algorithms that relay on one or both of atrial sensed events and ventricular sensed events. To that end, arrhythmia analyzer 98 may determine the ratio of atrial sensed events to ventricular sensed events (A/V ratio) (124).

If the A/V ratio (124) indicates there are less atrial sensed events than ventricular sensed events (126), then arrhythmia analyzer 98 classifies the cardiac episode as VT/VF. In the event that the number of atrial sensed events approximately equal the number of ventricular events (A=V) (130), the arrhythmia analyzer 98 applies logic (132) specific to cardiac episodes with an A=V ratio in order to classify the cardiac episode as VT/VF, inappropriate, or indeterminate (134). As discussed above, a classification by arrhythmia analyzer 98 as VT/VF confirms the episode classification by episode classifier 80 of IMD 16, a classification by arrhythmia analyzer 98 as inappropriate indicates arrhythmia analyzer 98 determined the cardiac episode was SVT and that IMD 16 inappropriately classified and treated the cardiac episode with a shock, and a classification as indeterminate indicates that arrhythmia analyzer 98 was unable to conclusively determine whether the cardiac episode was VT/VF or SVT.

If the A/V ratio (124) indicates that the number of atrial sensed events is greater than the number of ventricular sensed events (A>V)(136), then arrhythmia analyzer 98 applies logic (138) specific to cardiac episodes with an A>V ratio in order to classify the cardiac episode as VT/VF, inappropriate, or indeterminate (140). As discussed above, a classification by arrhythmia analyzer 98 as VT/VF confirms the episode classification by episode classifier 80 of IMD 16, a classification by arrhythmia analyzer 98 as inappropriate indicates arrhythmia analyzer 98 determined the cardiac episode was SVT and that IMD 16 inappropriately classified and treated the cardiac episode with a shock, and a classification as indeterminate indicates that arrhythmia analyzer 98 was unable to conclusively determine whether the cardiac episode was VT/VF or SVT.

Figure 7:
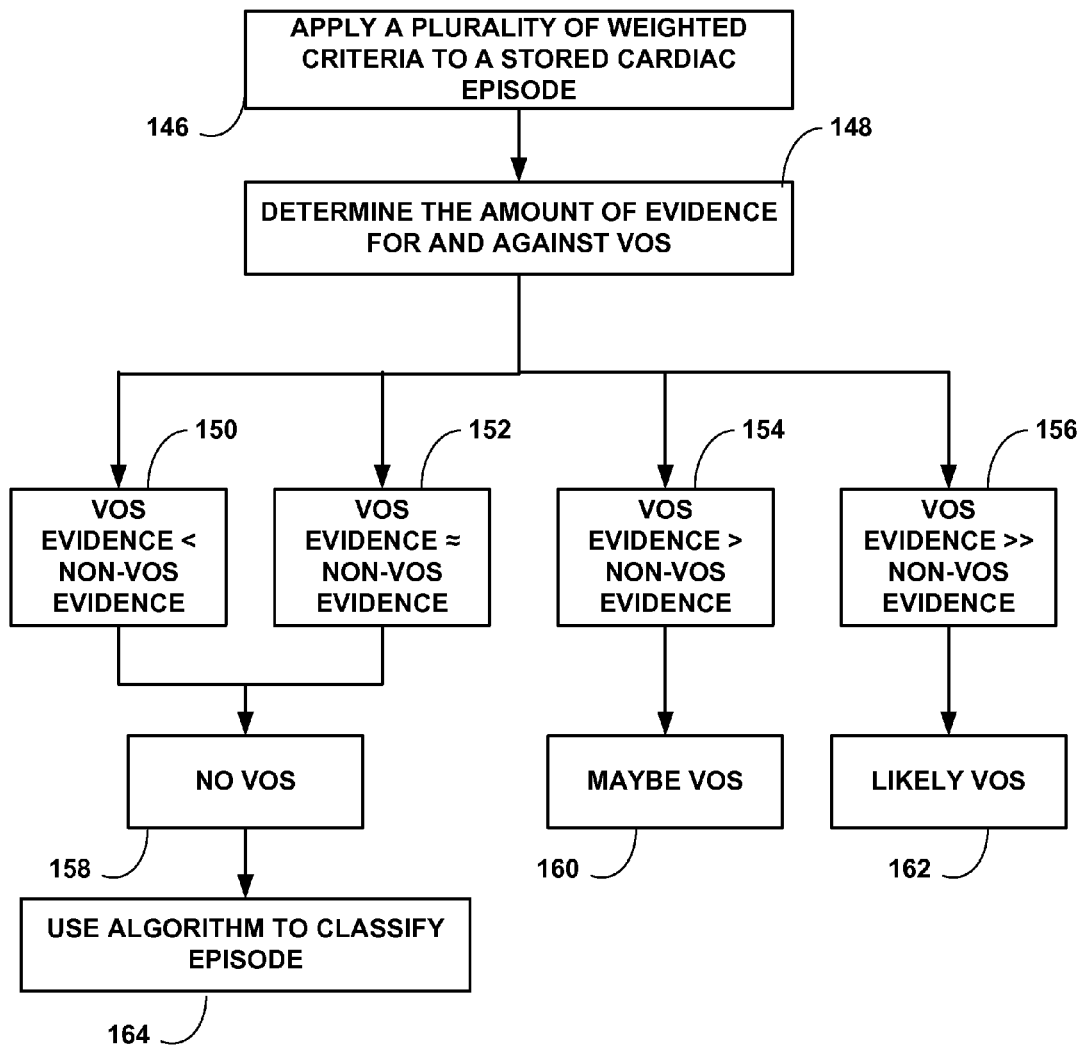
FIG. 7 is a flow diagram illustrating an example method of determining the presence of ventricular over-sensing (VOS) using probabilistic analysis.

FIG. 7 is a flow chart illustrating an example method of determining the presence of VOS using a probabilistic analysis. Although discussed with respect to implementation by arrhythmia analyzer 98, a probabilistic VOS algorithm such as the one discussed with respect to FIG. 7 may be implemented in real time by episode classifier 80 of IMD 16. In addition arrhythmia analyzer 98 may be located in any of a number of external devices. For example, the method may be implemented by external server 104, computing device 108, or programmer 24.

In some examples, arrhythmia analyzer 98 applies a plurality of weighted criteria a cardiac episode (146). The criteria may include consideration of the number of R-R intervals of certain lengths. For example, the number of R-R intervals with lengths less than 130 milliseconds (ms), the number of intervals with a length between 131 ms and 160 ms, the number of intervals with a length between 271 ms and 349 ms, and the number of intervals with a length greater than or equal to 350 ms.

The criteria may also include the regularity of ventricular intervals during the episode. In some examples, the episode may be classified as irregular, regular, or very regular, depending on the regularity of the ventricular intervals during the episode.

The regularity may be determined based on the consistency of interval lengths. For example, the regularity may be determined based on the cumulative differences between consecutive intervals. More particularly, the sum of the absolute values of the differences between the consecutive intervals prior to detection may be compared to one or more thresholds to classify the episode as regular, irregular, or very regular. In one example, the sum must be less than or equal to a first threshold to be classified as regular, and less than or equal to a second, lower threshold to be classified as very regular. The sum of the absolute values of the differences may be called a factor. For example, a factor of 6 would indicate that the sum of the difference for the intervals examined is 6 ms. In addition, in some examples, each consecutive change in interval length may not be greater than a threshold, such as 40 ms, for the episode to be considered regular.

To be considered extremely regular, 10 consecutive intervals are examined and the threshold to be considered extremely regular is a factor of 6. That is, for at least 10 consecutive intervals the sum of the absolute values of the differences between the consecutive intervals is less than 6 ms. For very regular episodes, 12 consecutive intervals are used and a factor of 14 is used as the threshold. For regular episodes, 10 consecutive intervals are used along with a factor of 25 for the threshold.

Arrhythmia analyzer 98 may additionally or alternatively determine whether an episode included a regular rhythm based on a comparison of an interval of an episode to the previous two intervals of the episode. In some examples, the determination of regularity may be made based in part on the equation:

$$\min(|(i-1)-i|/I, [(i-2)-i/I, |[(i-1)+(i-2)]-i|/i, |[(i-1)-(i-2)]|-i|/i)$$

Wherein, i equals the current interval, i−1 equals the previous interval, and i−2 equals the interval prior to i−1. A rhythm is considered regular if a preset number of the RR intervals just prior to detection of the arrhythmia have a value from the equation that falls below a preset threshold. In some examples, 7 out of 12 of the RR intervals must have a result from the equation of less than the threshold, e.g., less than approximately 0.12 or less.

The criteria may also include various criteria related to whether the EGM may have been influenced by electromagnetic interference or other noise sources. For example, the criteria may include the noise level of the EGM signal, whether there are bursts of noise in the EGM signal, or whether there is evidence of EGM saturation. The criteria for and against VOS may also include whether these is a sinusoidal pattern within the EGM, or whether the RR interval distribution is typical of VF. The criteria may also include whether baseline periods are present in the EGM signal of the cardiac episode, whether a far-field (FF) EGM signal associated with the cardiac episodes includes evidence of oversensing in the FF, the signal frequency content of the EGM signal, evidence of electromagnetic interference (EMI), or evidence of myopotentials. A baseline period is a period of a flat EGM signal. For example, the EGM signal includes, no activity and no noise sensed. The criteria may also include evidence of TWOS, which is discussed in more detail below with respect to FIG. 8. In some examples, the criteria may include evidence of R-wave over-sensing (RWOS), whether there is a pattern of RR (or VV) interval rate changes, and/or whether there is variation in slew within the episode. In some examples, the slew of a beat within the cardiac episode is the slope of the R-wave.

After arrhythmia analyzer 98 has analyzed the EGM signal for the cardiac episode for each of the criteria, the arrhythmia analyzer 98 determines the amount of evidence for and against VOS (148). Below is a list of possible uses of the criteria above with example weights used. The list and weights are not intended to be limiting. In some examples, if there are two or more intervals less than 160 ms in length, then a +1 is added to the evidence for VOS. If there are eleven or more intervals between 161 ms and 270 ms in length, then +1 is added to evidence of non-VOS. If there are more than six intervals with a length between 271 ms and 349 ms then +1 is added to the evidence of non-VOS. If there are more than seven intervals with a length of 350 ms or greater, then +1 is added to evidence of non-VOS. In some examples, the level of noisiness of the EGM signal is used as a factor for or against the presence of VOS. If arrhythmia analyzer 98 determines the EGM signal to be noisy, then +1 is added to VOS evidence. If arrhythmia analyzer 98 determines the EGM signal is very noisy or extremely noisy, then +2 is added to VOS evidence, if arrhythmia analyzer 98 determines there is EGM signal saturation, then +3 is added to VOS evidence, and if arrhythmia analyzer 98 determines the EGM signal is not noise, then +1 is added to non-VOS evidence. In some examples arrhythmia analyzer 98 may determine that a VOS pattern is present on the FF EGM signal. The presence of a VOS pattern on the FF EGM signal is a +3 for VOS evidence. If arrhythmia analyzer 98 determines that EMI is present then +3 is added to VOS evidence. If arrhythmia analyzer 98 determines that myopotenials are present in the EGM signal, then +3 is added to VOS evidence. In some examples, arrhythmia analyzer 98 analyzes the sinusoidal patter of the EGM signal on the FF EGM channel. If the slew is consistent for V beats on the FF EGM channel, then +1 for non-VOS evidence. If the slew is not consistent for V beats on the FF EGM channel, then +1 for VOS evidence. In some examples, arrhythmia analyzer 98 examines the RR distribution. If the RR distribution is not typical of VF, then +1 for VOS evidence.

Arrhythmia analyzer 98 may implement an algorithm to determine whether the EGM signal of the cardiac episode indicates TWOS. An example algorithm for detecting TWOS is described below with respect to FIG. 8. If arrhythmia analyzer 98 determines that TWOS is present, then +5 for VOS evidence. Arrhythmia analyzer 98 may also examine the EGM signal for the presence of RWOS. If RWOS is present, then +3 for VOS evidence.

Some factors may be evaluated in combination to determine whether to add weight to VOS evidence or to non-VOS evidence. For example, a combination of a number of intervals less than 130 ms and an irregular rhythm results in a +1 for evidence of VOS. The combination of a regular episode, a regular rhythm and no intervals under 130 ms results in a +1 for non-VOS. The combination of a low frequency EGM signal content, no EGM saturation and no evidence of TWOS results in a +4 for non-VOS. The combination of a sudden onset of fast VV rate that remains fast, no evidence of TWOS, and a VOS pattern not found on the FF EGM results in a +3 added to non-VOS evidence.

After arrhythmia analyzer 98 has applied preselected weighted criteria to the cardiac episode, arrhythmia analyzer 98 determines the total amount of evidence for and against VOS (148). This may be done by adding up the weighted factors indicating VOS and the weighted factors indicating no VOS separately. In some examples, the evidence of VOS may be given a positive weight while the weighted factors indicating no VOS may be subtracted from the total weight for VOS. For example, instead to +1 for non-VOS evidence as described above, 1 would be subtracted from VOS evidence for a criterion with a 1 weight being met for non-VOS. Arrhythmia analyzer 98 determines whether the VOS evidence is less than the non-VOS evidence (150), whether the VOS evidence is approximately equal to the non-VOS evidence (152), whether the VOS-evidence is greater than the non-VOS evidence (154) or whether the VOS evidence is much greater than the non-VOS evidence (156). If the VOS evidence is less than or approximately equal to the non VOS evidence, then arrhythmia analyzer 98 determines there was no VOS (158) present in the cardiac episode and proceeds to use one or more algorithms to classify the cardiac episode (164). If there is more evidence of VOS than evidence against VOS, arrhythmia analyzer 98 determines that the cardiac episode may include VOS (160). If there is much more evidence of VOS then of no VOS then arrhythmia analyzer 98 determines that the cardiac signal likely includes VOS (162).

Figure 8:
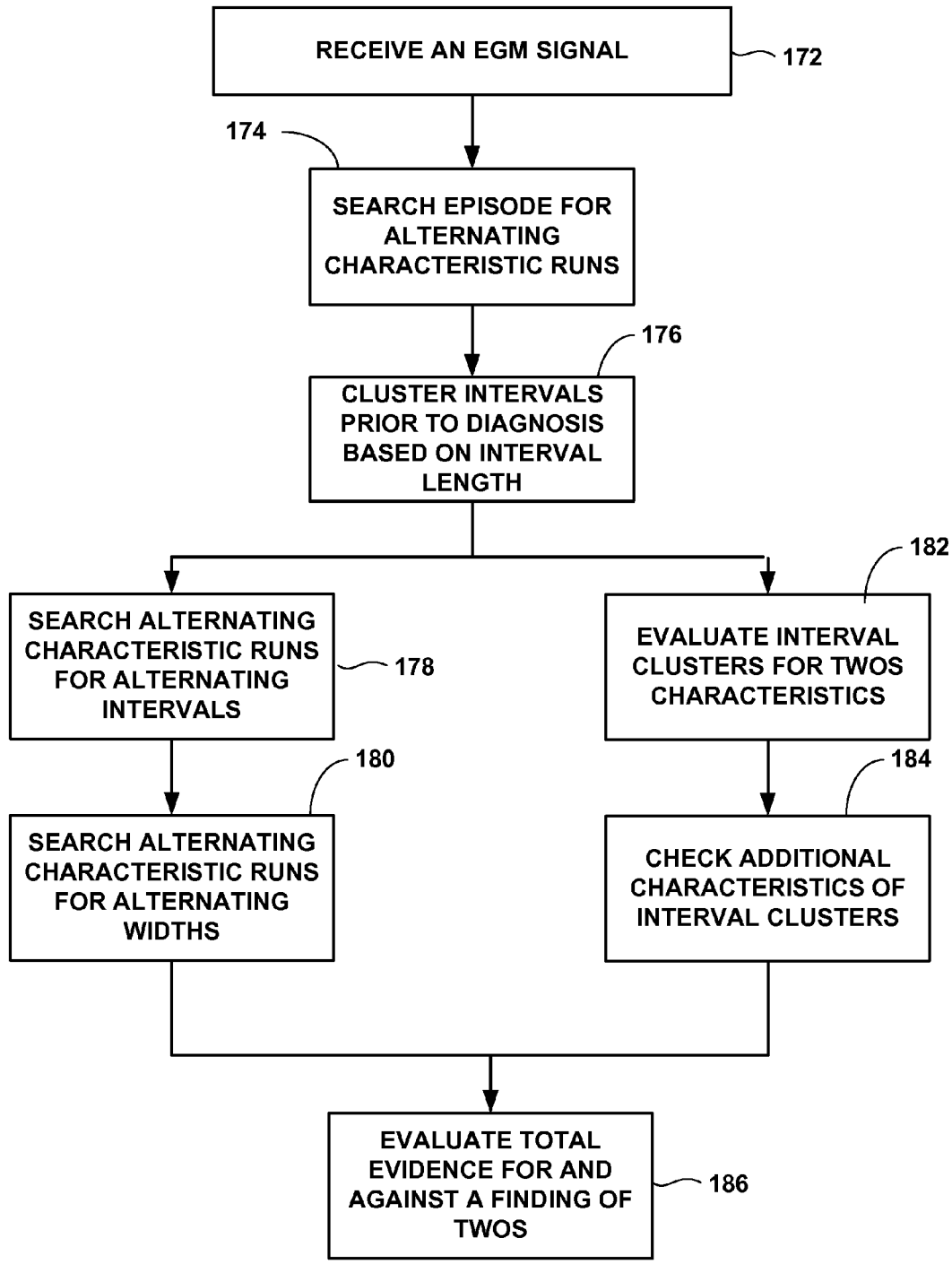
FIG. 8 is a flow diagram illustrating an example method of determining whether T-wave over-sensing (TWOS) is present in an EGM signal detected by an IMD.

FIG. 8 is a flow diagram illustrating an example method of determining whether T-TWOS is present in an EGM signal detected by IMD 16. In some examples, an algorithm for detecting TWOS may be used by episode classifier 80 during real time examination of an EGM signal for diagnosis of abnormal cardiac episodes. In some examples, arrhythmia analyzer 98 determines whether TWOS is present in a stored cardiac episode. The example illustrated in FIG. 8 is one in which arrhythmia analyzer 98 determines whether TWOS is present in a cardiac episode. However, it will be appreciated that episode classifier 80 may similarly perform the example method of FIG. 8.

The arrhythmia analyzer 98 receives an EGM signal (172) from memory 92 for analysis. The arrhythmia analyzer 98 searches the cardiac episode for the presence of runs of consecutive R-waves and/or R-R intervals with alternating characteristics (174). A run of alternating characteristic is a number of beats in a row within the cardiac episode in which a given beat within the has different characteristics than the beat immediately preceding the beat and beat immediately after the beat, and similar characteristics to the beat two prior to the beat and the beat two after the beat within the run. The alternating characteristics may be, for example, alternating R-wave morphology, slew rate, or amplitude. In some examples, arrhythmia analyzer 98 may look at a number of beats, e.g., 24, proceeding detection of an arrhythmia by cardiac episode classifier 80. The arrhythmia analyzer 98 may look for multiple different alternating runs within the cardiac episode. The arrhythmia analyzer 98 returns the longest runs starting from each starting beat position, e.g., starting positions 1 through 24. In some examples, runs may overlap. For example, a particular beat may be the starting beat for a run of alternating slew rates as well as a run of alternating amplitudes. Arrhythmia analyzer 98 returns the run which is the longest between the different runs starting from the same beat. Any shorter runs may be removed as redundant. In some examples, redundant runs may also be removed if there is almost complete overlap. For example, if a first run starts at beat 1 and lasts for 6 beats and a second run starts at beat 2 and last for 8 beats, the first run may be removed as redundant as there the is only one beat that is not overlapping.

Arrhythmia analyzer 98 also clusters RR intervals within the cardiac episode based on interval length (176). Arrhythmia analyzer 98 determines the length of each interval between each R-wave within the cardiac episode. Arrhythmia analyzer 98 then clusters, or sorts, the intervals into groups where the intervals within the group are close in value and where there is a distinct separation from values in other clusters.

For example, interval lengths between 180 ms and 210 ms may make up one cluster, while interval lengths between 240 ms and 270 ms are within another cluster. There may be no or very few intervals with lengths between 210 and 240 ms.

Arrhythmia analyzer 98 may cluster intervals by placing each interval value in an array of bins e.g., each bin including an X ms range, for example, and sorting the array. Arrhythmia analyzer 98 may then count the number of interval values in each bin, and then looks for bins or consecutive bins with no intervals, or only one interval. In some examples, a stretch of interval length value bins with no intervals or only one interval is considered a "dead zone," or an area between clusters. The dead zone may be between 5 and 25 ms in length. In some examples, the length of the stretch is programmable by a clinician or other user. In some examples, a default dead zone length may be approximately 10 ms.

Arrhythmia analyzer 98 then examines the possible clusters between the dead zones. In some examples, arrhythmia analyzer 98 may look for the average interval length value of the intervals within the cluster and the distribution around the average of the intervals within the clusters. The possible clusters may be broken up into additional clusters based on such a second sorting. In some examples, clusters with higher interval values may include a wider range of interval values than clusters with lower interval length values.

After clustering of interval values, arrhythmia analyzer 98 may examine the cardiac episodes in two ways. Arrhythmia analyzer 98 searches the alternating characteristic runs for alternating intervals (178). For example, arrhythmia analyzer 98 may determine whether the intervals within a run alternate with respect to into which cluster the intervals have been grouped. In some examples, arrhythmia analyzer 98 may consider a run to include alternating intervals if the run includes at least 3 alternating intervals. In some examples, the entire run examined includes alternating intervals. Arrhythmia analyzer 98 may provide a list of each of the runs with alternating intervals. Alternatively, in some examples, arrhythmia analyzer 98 may provide the longest run with alternating intervals. In some examples, arrhythmia analyzer 98 may keep a count of the total number of alternating intervals over the entire cardiac episode.

Arrhythmia analyzer 98 may also examine the alternating characteristic runs for alternating beat, e.g., R-wave widths (178). In some examples, arrhythmia analyzer 98 determines that there are not alternating widths if, for any of the beats, the difference between the current and previous width is less than 20% of the current width, or the difference between the current width and the second previous width is greater than 20%. In some examples, a count is keep of the number of alternating widths as each beat is examined, to determine the length of the run of alternative widths. In some examples, if the widths interval lengths remained alternating within the run for at least 2 beats, then the run is considered to include alternating widths. In some examples a cumulative count of the alternating widths is kept for each run.

Arrhythmia analyzer 98 may also examine interval clusters for TWOS characteristics (182). Arrhythmia analyzer 98 first identifies which cluster(s) have short intervals and which cluster has longer intervals. If there are two clusters, then one is labeled short and the other is labeled long. If there are three clusters, than one is labeled long and the other two are labeled short. Arrhythmia analyzer 98 determines if each cluster has more than two intervals. Arrhythmia analyzer 98 then determines if the shorter cluster(s) sum to equal the third. If there are two clusters, arrhythmia analyzer 98 determines the short cluster sums to the longer cluster if double the mean for the short cluster is close to the mean of the long cluster. In some examples, the sum must be within plus or minus a predetermined percentage of the longer cluster's mean interval length. In some examples the percentage may be approximately 6%.

If there are three clusters, then the means of the first short cluster and the second short cluster are summed. If the sum is close to the mean of the long cluster, the shorter clusters are considered to sum to the longer cluster. In some examples the sum is considered to be close if the sum is within plus or minus a predetermined percentage of the longer cluster's mean interval length. In some examples, the percentage may be approximately 6%. If the short cluster(s) sum to the longer cluster, arrhythmia analyzer 98 determines that the cardiac episode is displaying TWOS characteristics.

Arrhythmia analyzer 98 may check additional characteristics of the interval clusters (184). In some examples, arrhythmia analyzer 98 may determine if there are primarily two distinct clusters, and whether or not there if a single transition in time between one cluster and another. If there is a single transition this may be evidence that TWOS not present as such a transition may indicate a transition to VT or VF. Arrhythmia analyzer 98 may also determine if there are two distinct clusters. Arrhythmia analyzer 98 may determine there are two distinct clusters if the difference in the mean value of the clusters is greater than 150 ms. In addition there should be at least two switches between the clusters in the cardiac episode.

Arrhythmia analyzer 98 evaluates the total evidence for and against a finding of TWOS (186). In some examples, the evaluation of the total evidence is a probabilistic determination with each possible piece of evidence having a predetermined weight for or against a determination of TWOS.

For example, if arrhythmia analyzer 98 determined at the interval lengths where clustered into two distinct bands, then 4 points may be added to evidence for TWOS. If there is at least one run with alternating intervals for the length of the run, then 1 point is added to evidence for TWOS, and if there is not a run with alternating intervals for the length of the run, than 1 point is added to evidence against TWOS. If the longest run of alternating intervals is greater than or equal to five intervals and the maximum count for alternating interval lengths is greater than or equal to 3 intervals with alternating lengths, then 3 points are added to evidence for TWOS. If the longest run of alternating widths is greater than four intervals with alternating widths, then 2 points may be added to evidence for TWOS. If the cumulative count of alternating intervals is greater than or equal to eight alternating intervals, and the cumulative count for alternating widths interval lengths is greater than or equal to six, then 2 points may be added to evidence for TWOS. If the short interval cluster(s) were found to sum to the long interval cluster, than 2 points may be added to evidence of TWOS. On the other hand, if the short intervals were found to not sum to the long interval cluster, than 1 point may be added to evidence against TWOS. In some examples other characteristics, such as slew rate may also be used as evidence for TWOS if the characteristic alternates.

Arrhythmia analyzer 98 may also determine a modality for the cardiac episode based on number of and characteristics of RR interval length clusters. A cardiac episode may be considered unimodal, bimodal, multimodal or too diverse. Modality may be used to confirm or deny a categorization as TWOS and other types of VOS. If there is a single tight cluster of RR interval lengths, then the episode may be considered unimodal. If there is more than one cluster, arrhythmia analyzer 98 identifies the cluster with the highest number of intervals in it. If that cluster has less than one quarter of all intervals in the cardiac period, then there is no prominent cluster, and the modality is set to 0. If the cluster with the highest number of intervals has more than a threshold amount, e.g., 80%, of all the intervals of the cardiac episode, the cardiac episode is considered unimodal. If the two clusters with the highest counts together comprise more than a threshold amount, e.g., 75%, of all intervals in the cardiac episode, then arrhythmia analyzer 98 determines the cardiac episode is bimodal. Otherwise, if there is more than one cluster, arrhythmia analyzer 98 determines the cardiac episode is multimodal. A unimodal episode may be identified as TWOS and the modality may be set at 1. A bimodal episode may also be identified as TWOS. A multimodal episode with a mode of 3 may be an indication of oversensing including far-field R-waves or during cardiac resynchronization therapy. 4 or more modes may indicate that the intervals are too diverse to classify as a pattern of oversensing.

Figure 9:
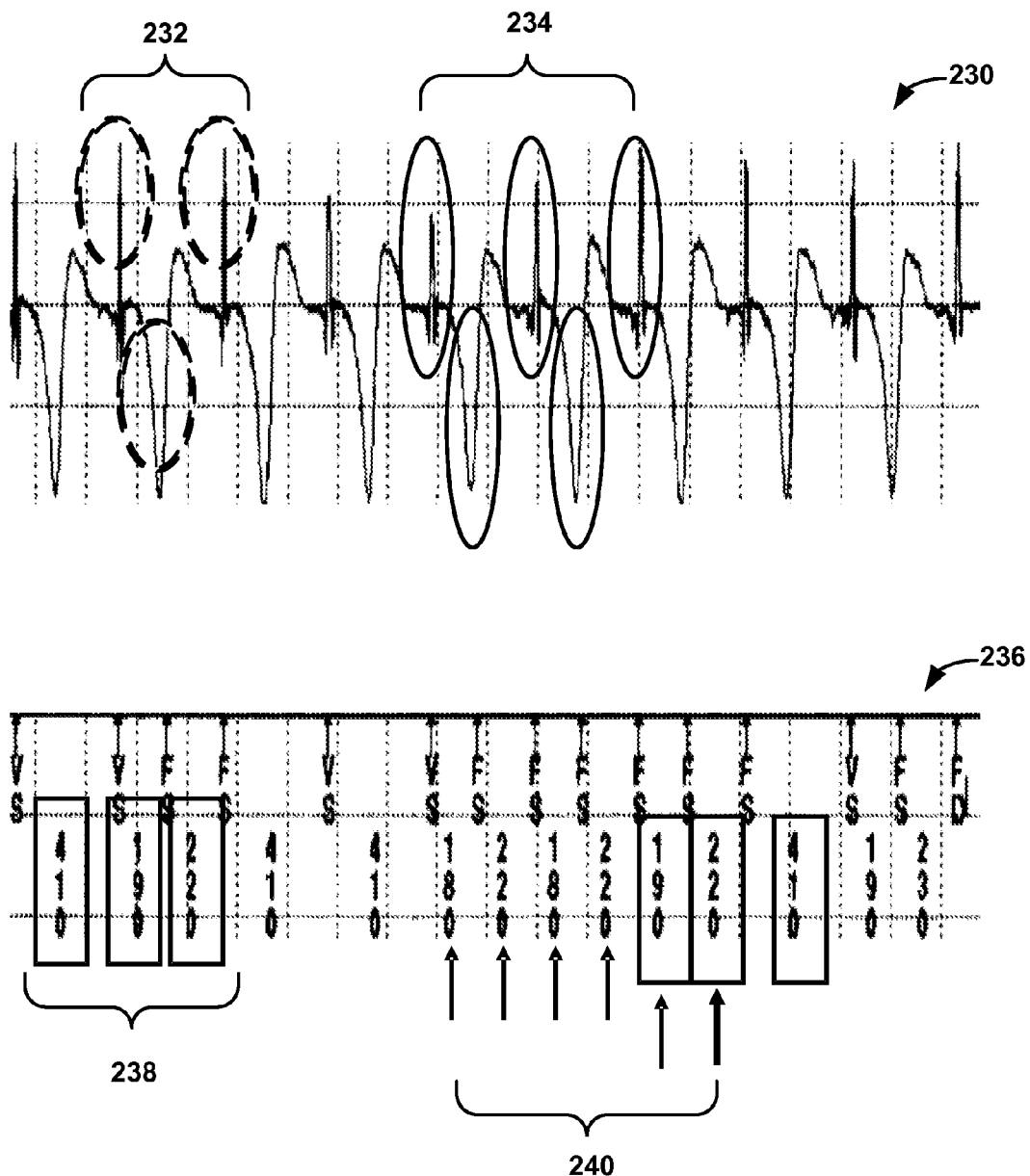
FIG. 9 illustrates an example EGM signal and marker channel with characteristics used to detect TWOS.

FIG. 9 illustrates example an example EGM signal 230 and marker channel 236 with characteristics used to detect TWOS. The EGM signal 230 includes beats with alternating slew rates 232. The beats with the alternating slew rates may be identified by the dashed circles. The EGM signal also includes beats with alternating morphology 234. The beats with the alternating morphology may be identified by the solid circles. Marker channel 236 includes consecutive intervals whose sum equals a third VV interval 238. The intervals are indicated by boxes. Marker channel 238 also includes alternating VV interval lengths 240 indicated by arrows.

Figure 10:
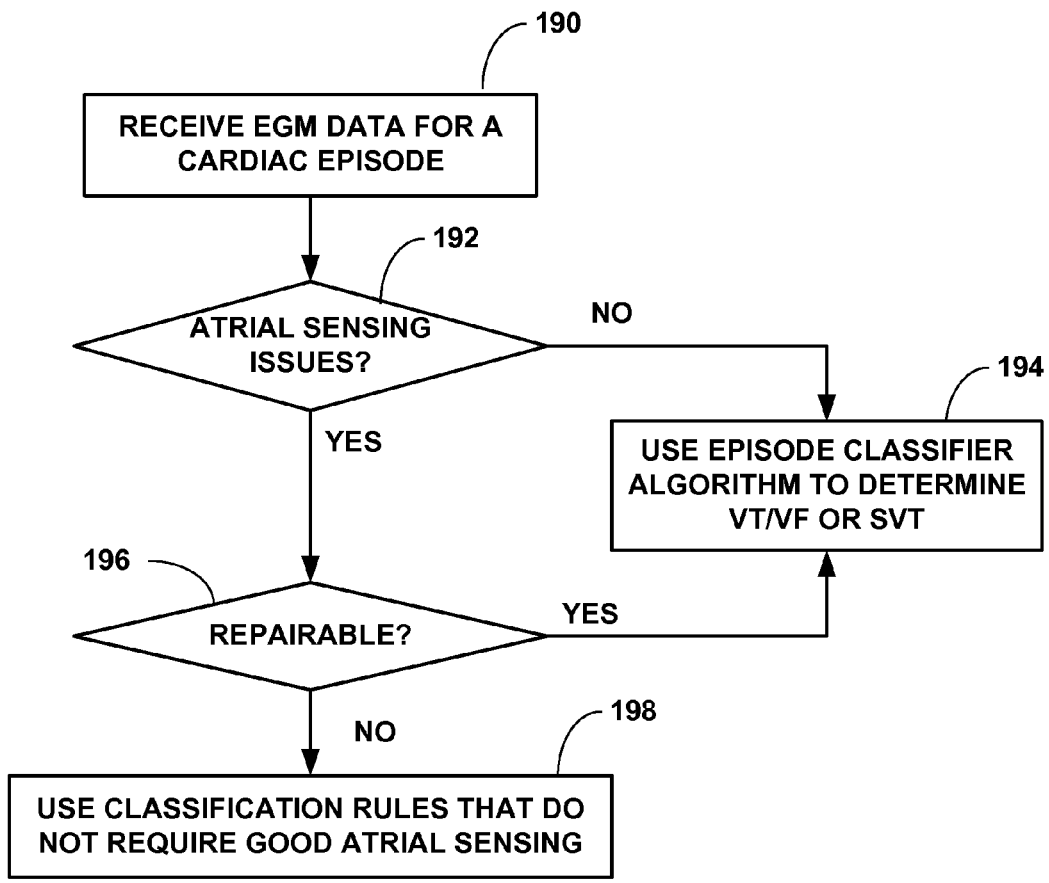
FIG. 10 is a flow diagram illustrating an example method of categorizing a cardiac episode including atrial sensing issues.

FIG. 10 is a flow chart illustrating an example method of categorizing a cardiac episode including atrial sensing issues. Although described as if implemented by arrhythmia analyzer 98, in some examples, the method may be implemented by processor 70 or episode classifier 80 of IMD 16.

According to the illustrated example, arrhythmia analyzer 98 receives EGM data for a cardiac episode (190). Arrhythmia analyzer 98 determines if the EGM data indicates the presence of atrial sensing issues (192). In some examples, arrhythmia analyzer 98 determines the presence of atrial sensing issues if the number of atrial sensed events is different on the near-field (NF) channel then on the far-field channel. In some examples, arrhythmia analyzer 98 determines that atrial sensing issues are present based on irregularity in AA intervals.

If there are not sensing issues, then arrhythmia analyzer 98 continues to analyze the EGM data using an episode classifier algorithm to determine whether there the cardiac episode is VT/VF or SVT (194). If arrhythmia analyzer 98 determines there is an atrial sensing issue, then arrhythmia analyzer 98 determines whether the atrial sensing issue is repairable (196). If there the sensing issue is repairable, for example because it is on only one channel, then arrhythmia analyzer 98 fixes the sensing issue in the EGM signal data and uses an episode classifier algorithm to determine if the cardiac episode is VT/VF or SVT (194). If the atrial sensing issues are not repairable, then arrhythmia analyzer 98 uses classification rules that do not require good atrial sensing (198). In some examples, the classification rules that do not require good atrial sensing may include whether RR intervals are extremely regular or fast, whether AF characteristics are displayed, whether the rhythm after pacing VT/VF, the frequency of the ventricular signal, and ventricular morphology rules.

In some examples, the rules for RR intervals being extremely regular or fast may be different than those used by arrhythmia analyzer 98 to determine whether VOS is present. In some examples, arrhythmia analyzer 98 categorizes the cardiac episode as VT/VF is any of the following criteria related to the RR intervals of the episode being regular and fast are met:

at least 10 intervals in a row that are with any change between each consecutive interval less than 40 ms and the absolute value difference between the intervals is less than or equal to a threshold factor of 14 at least 10 consecutive intervals, the absolute value of the differences between the intervals is less than or equal to a threshold factor of 25 and a median VV interval length of less than 270 ms.

If the median VV interval length prior to detection or diagnosis is less than 200 ms.

Although specific thresholds values are disclosed, other cut-offs or methods of determining regularity may be used. In general more regularity is expected as the rate increases. If the cardiac episode does not meet any of the criteria for being considered regular or fast, then arrhythmia analyzer 98 determines if the cardiac episode includes atrial fibrillation (AF) characteristics. In some examples, the determination of whether AF characteristics are present is based on the method of FIG. 10, discussed below. If arrhythmia analyzer 98 determines that AF characteristics are present, then the cardiac episode is classified as SVT.

If there cardiac episode does not display AF characteristics, then arrhythmia analyzer 98 determines if the rhythm after pacing is VT/VF. If the rhythm after pacing is VT/VF then the cardiac episode is classified as VT/VF. If the cardiac episode is not classified based on the after pacing rhythm, then arrhythmia analyzer 98 may classify the cardiac episode as VT/VF based on a low-frequency ventricular signal. In some examines, arrhythmia analyzer 98 may determine the mean frequency content of the ventricular signal. The cutoff to be determined VT/VF may be around approximately 6 Hz. In some examples, a cardiac episode including a period of ventricular pacing may additionally or alternatively be classified based on an analysis of the arrhythmia after pacing.

Arrhythmia analyzer 98 may also use ventricular morphology rules to classify the cardiac episode as VT/VF or SVT. In some examples, the ventricular beats, e.g., R-waves, in the cardiac episode may be compared to one or more templates. For example, the beats may be compared to a VT template and to a SVT template. If a predetermined percentage of the beats in the cardiac episode are found to match one of the templates, then the cardiac episode is classified as either VT/VF or SVT. In the event that none of the rules result in a classification of the episode, the cardiac episode is classified as unknown or indeterminate.

Figure 11:
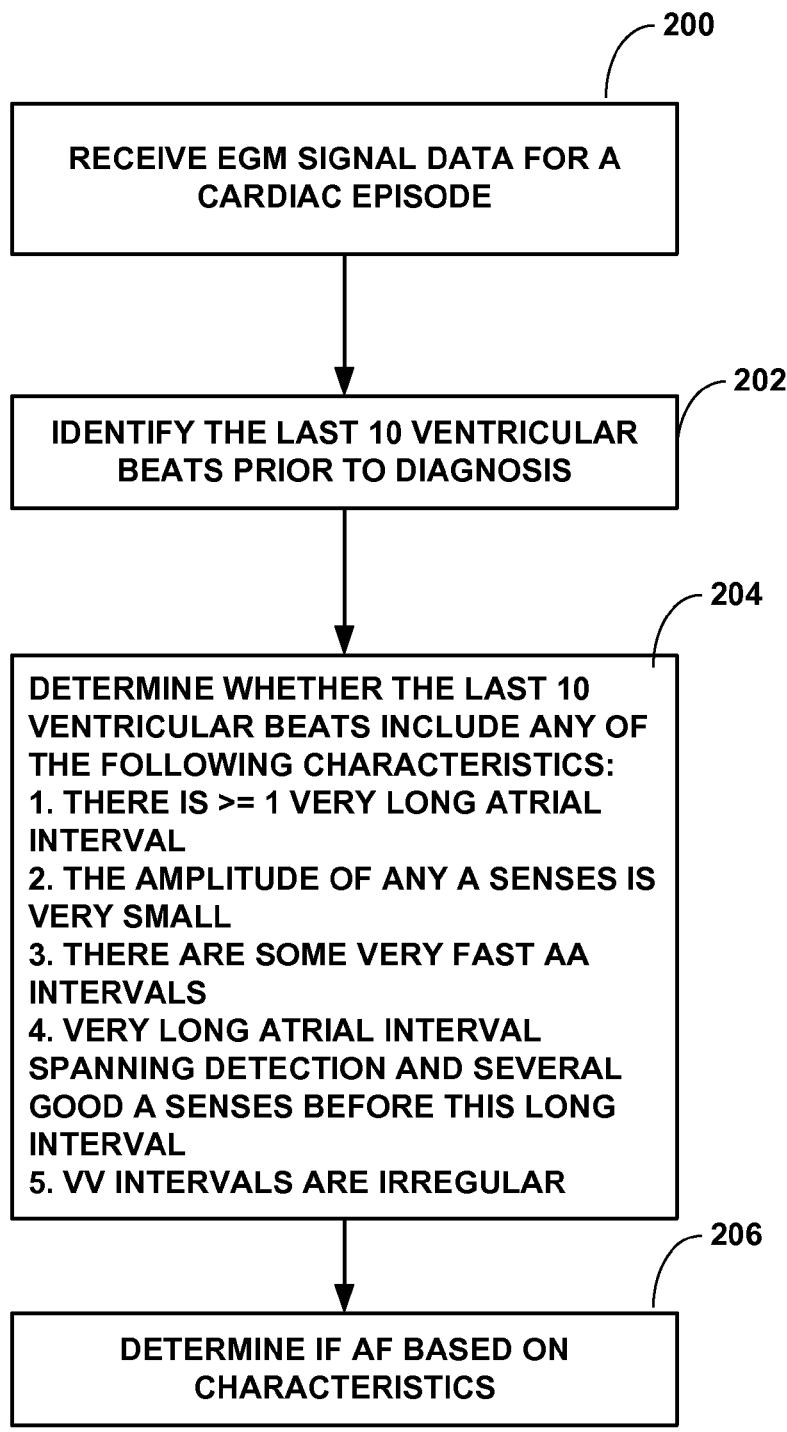
FIG. 11 is a flow diagram illustrating an example method of classifying a cardiac episode as including atrial fibrillation (AF).

FIG. 11 is an example method of classifying a cardiac episode as including atrial fibrillation (AF). Although described with respect to arrhythmia analyzer 98 in an external device, processor 70 or episode classifier 80 of IMD 16 may use similar characteristics to classify a cardiac episode as AF at the time of diagnosis.

According to the example method, arrhythmia analyzer 98 receives EGM signal data for a cardiac episode (200). Arrhythmia analyzer 98 then identifies the last 10 ventricular beats prior to diagnosis by IMD 16 (202). Arrhythmia analyzer 98 then scrutinizes the 10 beats to determine whether the last 10 ventricular beats include any of the following characteristics:

1. There is greater than or equal to 1 very long atrial interval
2. The amplitude of any atrial sensed event is very small
3. There are some very fast AA intervals
4. There is a very long atrial interval spanning detection by IMD 16 and several good atrial sensed events prior to the long interval
5. The VV intervals are irregular (204).

In some examples, an interval is considered very long if the length of the interval is greater than approximately 1800 ms. The amplitude of a sensed atrial event may be considered very small is the amplitude is less than approximately 2 millivolts. In some examples, the cardiac episode is considered to have fast AA intervals if at least 3 of the 10 intervals have an interval length below a predetermined threshold. The threshold may be approximately 200 ms, for example.

Arrhythmia analyzer 98 determines if the cardiac episode is AF based on the characteristics (206). In some examples, if 3 out of the 5 characteristics are met, then the cardiac episode is considered to be AF. In some examples, arrhythmia analyzer 98 may determine that there is even a higher likelihood of the cardiac episode is AF if there is normal atrial sensing at termination of the episode. Normal atrial sensing may be defined as at least 5 good atrial sensed events at termination and no atrial intervals greater than 1800 ms in the last 5 atrial beats. In some examples, if 2 out of 3 of characteristics 1-3 are found or characteristic 5 is true in addition to normal atrial sensing at termination, then the cardiac episode may be categorized as AF.

Figure 12:
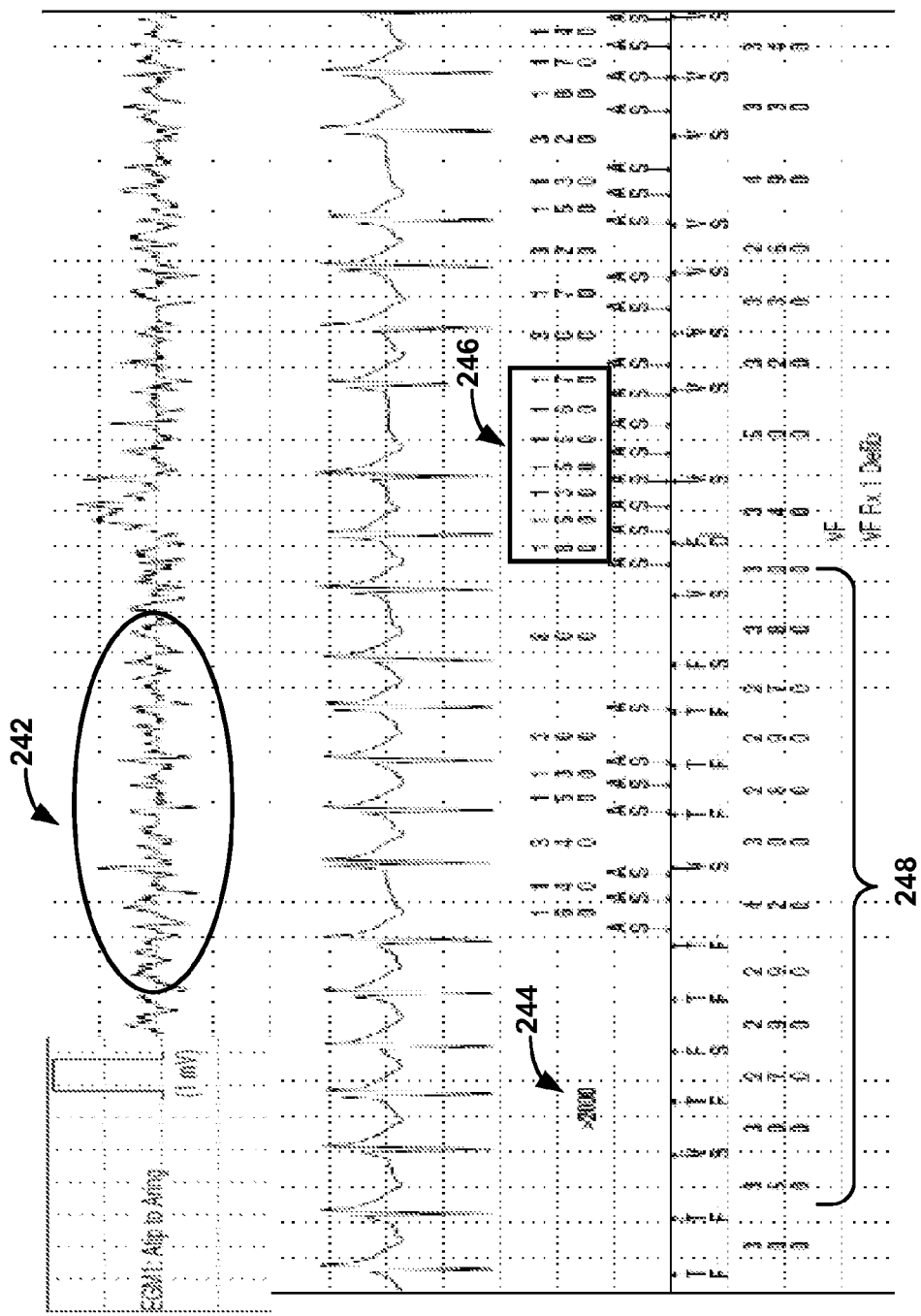
FIG. 12 illustrates an example EGM signal and marker channel showing AF characteristics.

FIG. 12 illustrates an example EGM signal and marker channel showing AF characteristics. The EGM signal includes portions with low atrial amplitude 242. The signal also include a long period with not atrial sensing 244, irregular VV interval lengths 248, and very fast atrial intervals 246. The characteristics shown in FIG. 12 may be used in the example method of FIG. 11 to determine if a cardiac episode includes AF.

Figure 13:
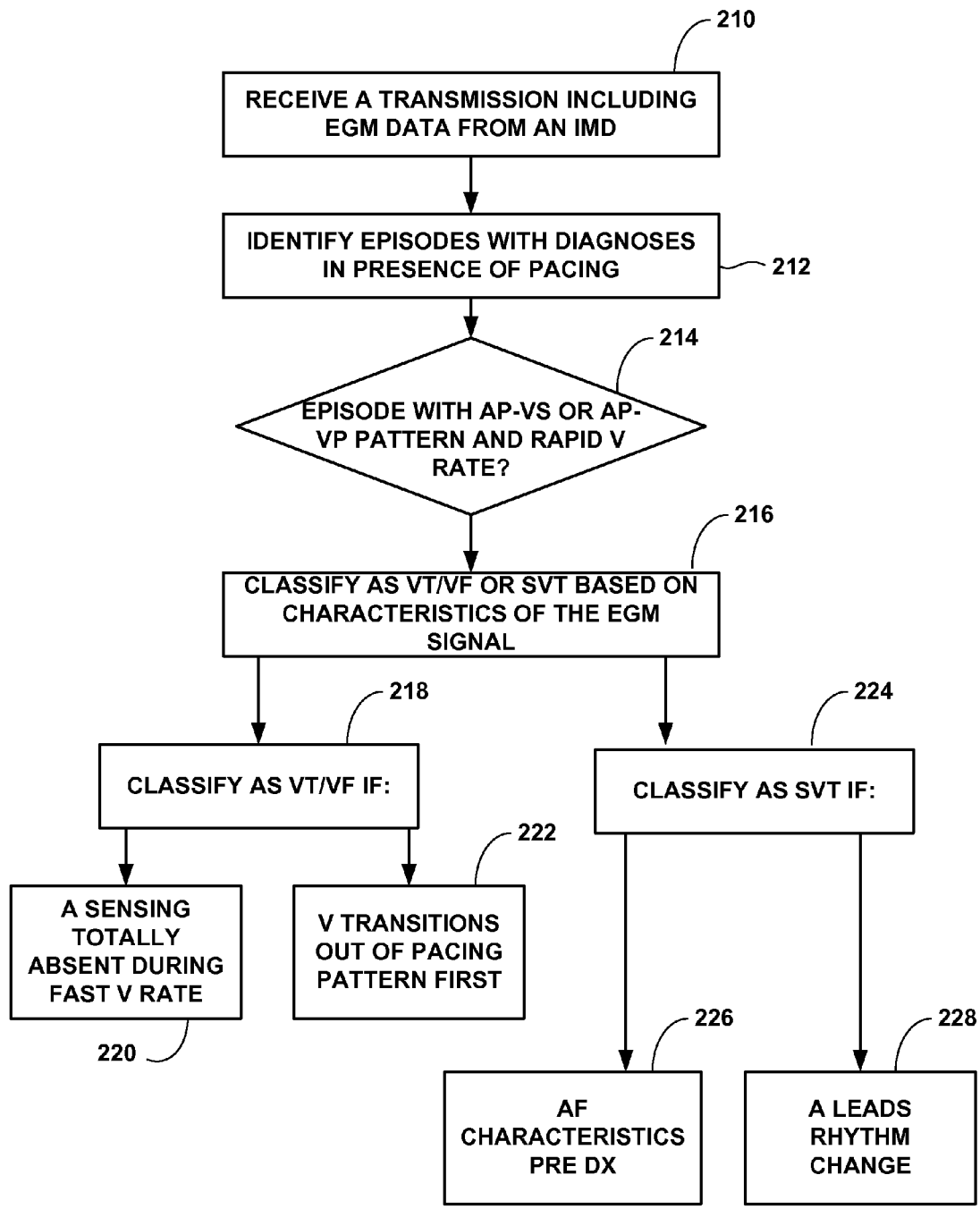
FIG. 13 is a flow diagram illustrating an example method of classifying a high-rate rhythm arising immediately after pacing.

FIG. 13 is a flow chart illustrating an example method of classifying a high-rate rhythm arising after pacing. In some examples, the high-rate rhythm arises within a predetermined number of beats of pacing. In some examples the high-rate rhythm arises immediately after pacing. The pacing may be, for example, cardiac resynchronization therapy (CRT).

An external device such as programmer 24 receives a transmission including EGM data from IMD 16 (210). Arrhythmia analyzer 98 may identify episodes in the transmission with diagnoses of tachyarrhythmia in the presence of pacing (212). Arrhythmia analyzer 98 may examine identified episodes to determine whether a particular episode has either an atrial paced-ventricular sensed or an atrial paced-ventricular paced pattern and a rapid ventricular rate (214) followed by detection and diagnosis as VT/VF. Arrhythmia analyzer 98 may then classify as VT/VF or SVT based on the characteristics of the EGM signal (216) of the cardiac episode. Arrhythmia analyzer 98 classifies the cardiac episode as VT/VF (218) and appropriately classified by IMD 16 if: A sensing is totally absent during fast V rate (220) prior to detection and atrial pacings are present at termination. Such a pattern is indicative of an atrial pacing dependent patient. The cardiac episode may also classified as VT/VF if (218) the AA intervals and VV intervals are relatively regular and similar prior to diagnosis and the ventricles transition out of the pacing pattern first (222).

Arrhythmia analyzer 98 may classify the cardiac episode as SVT (224) and improperly diagnosed by the IMD if AF characteristics exist pre-diagnosis. In some examples, arrhythmia analyzer 98 may determine if AF characteristics exist based on the method of FIG. 11. Arrhythmia analyzer 98 may classify the cardiac episode as SVT (224) if the AA intervals and VV intervals are relatively regular and similar prior to diagnosis and the atria leads the rhythm change (228) after pacing.

The techniques described in this disclosure may be implemented, at least in part, in hardware, software, firmware, or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples have been described. These and other examples are within the scope of the following claims.

What is claimed is:

1. A method comprising:
receiving EGM signal data for a cardiac episode detected by an implantable medical device (IMD), wherein the EGM signal data includes at least ventricular sensed events and atrial sensed events;
determining, using a probabilistic analysis, whether the EGM signal data indicates ventricular over-sensing (VOS), wherein a determination that the EGM signal data indicates VOS further comprises classifying the cardiac episode as inappropriately shocked;
determining, when there is a determination that the EGM signal data does not indicate VOS, whether the EGM signal data indicates an atrial sensing issue, the atrial sensing issue including one of atrial over-sensing or atrial under-sensing, wherein:
when there is a determination of the atrial sensing issue, the method further comprises determining whether the atrial sensing issues are repairable;
when there is a determination that the atrial sensing issues are repairable, the method further comprises repairing the sensing issues and classifying the cardiac episode based on a set of classification rules that consider both the ventricular and atrial sensed events;
when there is a determination that the atrial sensing issues are not repairable, the method further comprises classifying the cardiac episode based on at least one classification rule that considers the ventricular sensed events but not the atrial sensed events; and
the classification of the cardiac episode based on a set of classification rules that consider both the ventricular and atrial sensed events, and the classification of the cardiac episode based on at least one classification rule that considers the ventricular sensed events but not the atrial sensed events comprises one of ventricular tachycardia/ventricular fibrillation, inappropriately shocked, or indeterminate.

2. The method of claim 1, wherein, the determining, based on the probabilistic analysis, whether the EGM signal data indicates VOS comprises:
determining, based on a probabilistic analysis, whether the EGM signal data indicates T-wave over-sensing (TWOS).

3. The method of claim 1, wherein the determining, based on the probabilistic analysis, whether the EGM signal data indicates VOS comprises:
evaluating each of a plurality of VOS criteria for the cardiac episode; calculating a VOS evidence value based on the evaluation of each of the plurality of VOS criteria, wherein a first one of the plurality of VOS criteria is given a first non-zero weight and a second one of the plurality of VOS criteria is given a second, different, non-zero weight;
identifying the cardiac episode, based at least on the VOS value, as non-VOS, or VOS; and
classifying the cardiac episode, in response to a non-VOS identification, based on one or more classification rules.

4. The method of claim 3, wherein the ventricular over-sensing criteria include criteria weighted against a finding of ventricular over-sensing, the criteria weighted against a finding of ventricular over-sensing comprising:
at least a first predetermined number of intervals between approximately 160 ms and approximately 270 ms;
at least a second predetermined number of intervals between approximately 270 ms and approximately 350 ms;
less than a third predetermined number of intervals greater than approximately 350 ms;
consistent slew rate for the sensed ventricular events;
a first combination of
a low frequency content EGM signal,
no evidence of EGM saturation, and
a determination of no TWOS;
a second combination of
a sudden onset of V to V interval rate change wherein the V to V interval rate increases and remains at an increased level,
a determination of no TWOS, and
no VOS found on a far-field EGM signal; and
a third combination of
a determination of a regular episode
a determination of a regular rhythm; and
no intervals less than or equal to approximately 130 ms;
wherein at least the first combination, the second combination, and the third combination are each given different weights.

5. The method of claim 3, wherein the ventricular over-sensing criteria includes criteria weighted for a finding of ventricular over-sensing, the criteria weighted for a finding of ventricular over-sensing comprising:
a determination of TWOS;
a finding of R-wave over-sensing (RWOS); and
inconsistent slew rate for the ventricular sensed events;
wherein the determination of TWOS, the finding of RWOS and inconsistent slew rate for ventricular sensed events are each given different weights.

6. The method of claim 3, further comprising detecting an EGM noise level, wherein the EGM noise level comprises one of not noisy, noisy, very noisy, extremely noisy or saturation, wherein the EGM noise level is evidence for or against a finding of VOS, and wherein the EGM noise level of noisy has a different weight of evidence than the EGM noise level of very noisy.

7. The method of claim 1, wherein the at least one classification rule that considers the ventricular sensed events but not the atrial sensed events is at least one of:
V-V interval extremely regular,
fast V-V interval,
rhythm after pacing is VT/VF,
low-frequency V signal,
ventricular morphology rules; and
atrial fibrillation (AF) characteristics.

8. The method of claim 1, wherein classification of the cardiac episode further comprising determining whether the cardiac episode indicates atrial fibrillation (AF), the determination comprising:
identifying a predetermined number of ventricular sensed events immediately prior to diagnosis by the IMD;
determining whether the EGM signal data spanning the predetermined number of ventricular sensed events includes one or more AF characteristics, the AF characteristics including:
at least one atrial interval greater than a first predetermined threshold,
an amplitude for any atrial sensed events less than a second predetermined threshold,
at least one atrial interval less than a third predetermined interval;

an atrial interval spanning diagnosis and greater in length than the first predetermined interval, or irregular ventricular intervals; and classifying the cardiac episode, based on the determined characteristics, as AF.

9. The method of claim 8, wherein the cardiac episode is classified as AF in response to a determination that at least 3 of the AF characteristics have been met.

10. The method of claim 8, wherein the first predetermined threshold is approximately 1800 ms.

11. The method of claim 8, wherein the second predetermined threshold is approximately 2 millivolts.

12. The method of claim 8, wherein the third predetermined threshold is approximately 200 ms.

13. The method of claim 8, wherein the cardiac episode is classified as AF in response to irregular intervals and normal atrial sensing at termination, wherein normal atrial sensing at termination includes at least five atrial sensed events prior to termination and no atrial intervals greater than approximately 1800 ms in the five atrial sensed events.

14. The method of claim 1, further comprising determining whether the cardiac episode includes a diagnosis of a of a tachyarrhythmia by the implantable medical device in the presence of pacing;

determining if the EGM signal data indicates the cardiac episode includes a rapid ventricular rate and atrial pacing; and classifying the cardiac episode as ventricular tachycardia/ventricular fibrillation (VT/VF) or supraventricular tachycardia (SVT) based on the EGM signal data, wherein classifying the cardiac episode comprises:

classifying the cardiac episode as VT/VF in response to the cardiac episode including at least one of: a period of fast ventricular rate with no atrial sensing, or an indication of the ventricle transitioning out of a pacing pattern first; and classifying the cardiac episode as SVT in response to the cardiac episode including at least one of: atrial fibrillation characteristics prior to a diagnosis by the implantable medical device, or an indication of the atria transitioning out of the pacing pattern first.

15. A system comprising:

a communication module configured to receive EGM signal data for a cardiac episode detected by an implantable medical device (IMD), wherein the EGM signal data includes at least ventricular sensed events and atrial sensed events; and a processor configured to:

determine, using a probabilistic analysis, whether the EGM signal data indicates ventricular over-sensing (VOS), wherein the determination is based at least in part on a probabilistic determination of whether the EGM signal data indicates T-wave over-sensing (TWOS) and wherein a determination of VOS further comprises classifying the cardiac episode as inappropriately shocked;

determine, when there is a determination of no VOS, whether the EGM signal data indicates an atrial sensing issue, the atrial sensing issue including one of atrial over-sensing or atrial under-sensing, wherein when there is a determination of the atrial sensing issue, determine whether the atrial sensing issues are repairable, when there is a determination that the atrial sensing issues are repairable, repair the sensing issues and classifying the cardiac episode based on a set of classification rules that consider both the ventricular and atrial sensed events;

when there is a determination that the atrial sensing issues are not repairable, classify the cardiac episode based on at least one classification rule that considers the ventricular sensed events but not the atrial sensed events; and wherein the classification based on a set of classification rules that consider both the ventricular and atrial sensed events, and the classification of the cardiac episode based on at least one classification rule that considers the ventricular sensed events but not the atrial sensed events comprises ventricular tachycardia/ventricular fibrillation, inappropriately shocked, or indeterminate.

16. The system of claim 15, wherein the processor is further configured perform the probabilistic analysis of VOS by evaluating each of a plurality of ventricular over-sensing criteria for the cardiac episode;

calculating a ventricular over-sensing evidence value based on the evaluation of each of the plurality of ventricular over-sensing criteria, wherein a first one of the plurality of ventricular over-sensing criteria is given a first non-zero weight and a second one of the plurality of ventricular over-sensing criteria is given a second, different, non-zero weight;

identifying the cardiac episode, based at least on the ventricular over-sensing value, as non-ventricular over-sensing, maybe ventricular over-sensing, or likely ventricular over-sensing; and classifying the cardiac episode, in response to a non-ventricular over-sensing identification, based on the set of classification rules.

17. The system of claim 16, wherein the ventricular over-sensing criteria includes criteria weighted against a finding of ventricular over-sensing, the criteria weighted against a finding of ventricular over-sensing comprising:

at least a first predetermined number of intervals between approximately 160 ms and approximately 270 ms;

at least a second predetermined number of intervals between approximately 270 ms and approximately 350 ms;

less than a third predetermined number of intervals greater than approximately 350 ms;

consistent slew rate for the sensed ventricular events;

a first combination of a low frequency content EGM signal, no evidence of EGM saturation, and a determination of no TWOS;

a second combination of a sudden onset of V to V interval rate change wherein the V to V interval rate increases and remains at an increased level, a determination of no TWOS, and no VOS found on a far-field EGM signal; and a third combination of a determination of a regular episode a determination of a regular rhythm; and no intervals less than or equal to approximately 130 ms;

wherein the processor is further configured to give each of at least the first combination, the second combination, and the third combination different weights.

18. The system of claim 16, wherein the ventricular over-sensing criteria includes criteria weighted for a finding of ventricular over-sensing, the criteria weighted for a finding of ventricular over-sensing comprising:
- a determination of TWOS;
- a finding of R-wave over-sensing (RWOS); and
- inconsistent slew rate for the ventricular sensed events;
- wherein the processor is further configured to give the determination of TWOS, the finding of RWOS, and inconsistent slew rate for ventricular sensed events each different weights.

19. The system of claim 16, wherein the processor is further configured to detect an EGM noise level, wherein the EGM noise level comprises one of not noisy, noisy, very noisy, extremely noisy or saturation, wherein the EGM noise level is evidence for or against a finding of VOS, and wherein processor is further configured to give the EGM noise level of noisy a different weight of evidence than the EGM noise level of very noisy.

20. The system of claim 15, wherein the at least one classification rule that considers the ventricular sensed events but not the atrial sensed events is at least one of:
- V-V interval extremely regular,
- fast V-V interval,
- rhythm after pacing is VT/VF,
- low-frequency V signal,
- ventricular morphology rules; and
- atrial fibrillation (AF) characteristics.

21. The system of claim 15, wherein the processor is further configured to determine whether the cardiac episode indicates atrial fibrillation (AF), the determination comprising:
- identifying a predetermined number of ventricular sensed events immediately prior to diagnosis by the IMD;
- determining whether the EGM signal data spanning the predetermined number of ventricular sensed events includes one or more AF characteristics, the AF characteristics including:
  - at least one atrial interval greater than a first predetermined threshold,
  - an amplitude for any atrial sensed events less than a second predetermined threshold,
  - at least one atrial interval less than a third predetermined interval;
  - an atrial interval spanning diagnosis and greater in length than the first predetermined interval, or
  - irregular ventricular intervals; and
- classifying the cardiac episode, based on the determined characteristics, as AF.

22. The system of claim 21, wherein the cardiac episode is classified as AF in response to a determination that at least 3 of the AF characteristics have been met.

23. The system of claim 21, wherein the first predetermined threshold is approximately 1800 ms.

24. The system of claim 21, wherein the second predetermined threshold is approximately 2 millivolts.

25. The system of claim 21, wherein the third predetermined threshold is approximately 200 ms.

26. The system of claim 21, wherein the processor is further configured to classify the cardiac episode as AF in response to irregular intervals and normal atrial sensing at termination, wherein normal atrial sensing at termination includes at least five atrial sensed events prior to termination and no atrial intervals greater than approximately 1800 ms in the five atrial sensed events.

27. The system of claim 15, wherein the processor is further configured to:
- determine whether the cardiac episode includes a diagnosis of a of a tachyarrhythmia by the implantable medical device in the presence of pacing;
- determine if the EGM signal data indicates the cardiac episode includes a rapid ventricular rate and atrial pacing; and
- classify the cardiac episode as ventricular tachycardia/ventricular fibrillation (VT/VF) or supraventricular tachycardia (SVT) based on the EGM signal data, wherein classifying the cardiac episode comprises:
  - classify the cardiac episode as VT/VF in response to the cardiac episode including at least one of: a period of fast ventricular rate with no atrial sensing, or an indication of the ventricle transitioning out of a pacing pattern first; and
  - classify the cardiac episode as SVT in response to the cardiac episode including at least one of: atrial fibrillation characteristics prior to a diagnosis by the implantable medical device, or an indication of the atria transitioning out of the pacing pattern first.

28. A system comprising:
- means for receiving EGM signal data for a cardiac episode detected by an implantable medical device (IMD), wherein the EGM signal data includes at least ventricular sensed events and atrial sensed events;
- means for determining, using a probabilistic analysis, whether the EGM signal data indicates ventricular over-sensing (VOS), wherein a determination that the EGM signal data indicates VOS further comprises classifying the cardiac episode as inappropriately shocked;
- means for determining, when there is a determination that the EGM signal data does not indicate VOS, whether the EGM signal data indicates an atrial sensing issue, the atrial sensing issue including one of atrial over-sensing or atrial under-sensing, wherein:
  - when there is a determination of the atrial sensing issue, the method further comprises determining whether the atrial sensing issues are repairable;
  - when there is a determination that the atrial sensing issues are repairable, the method further comprises repairing the sensing issues and classifying the cardiac episode based on a set of classification rules that consider both the ventricular and atrial sensed events;
  - when there is a determination that the atrial sensing issues are not repairable, the method further comprises classifying the cardiac episode based on at least one classification rule that considers the ventricular sensed events but not the atrial sensed events; and
  - the classification of the cardiac episode based on a set of classification rules that consider both the ventricular and atrial sensed events, and the classification of the cardiac episode based on at least one classification rule that considers the ventricular sensed events but not the atrial sensed events comprises one of ventricular tachycardia/ventricular fibrillation, inappropriately shocked, or indeterminate.

29. A non-transitory computer-readable medium comprising instructions for causing a programmable processor to:
- receive EGM signal data for a cardiac episode detected by an implantable medical device (IMD), wherein the EGM signal data includes at least ventricular sensed events and atrial sensed events;
- determine, using a probabilistic analysis, whether the EGM signal data indicates ventricular over-sensing (VOS), wherein the determination is based at least in part on a probabilistic determination of whether the EGM signal data indicates T-wave over-sensing (TWOS) and wherein a determination of VOS further comprises classifying the cardiac episode as inappropriately shocked;

determine, when there is a determination of no VOS, whether the EGM signal data indicates an atrial sensing issue, the atrial sensing issue including one of atrial over-sensing or atrial under-sensing, wherein when there is a determination of the atrial sensing issue, determine whether the atrial sensing issues are repairable, when there is a determination that the atrial sensing issues are repairable, repair the sensing issues and classifying the cardiac episode based on a set of classification rules that consider both the ventricular and atrial sensed events;

when there is a determination that the atrial sensing issues are not repairable, classify the cardiac episode based on at least one classification rule that considers the ventricular sensed events but not the atrial sensed events; and wherein the classification of the cardiac episode based on a set of classification rules that consider both the ventricular and atrial sensed events, and the classification of the cardiac episode based on at least one classification rule that considers the ventricular sensed events but not the atrial sensed events comprises ventricular tachycardia/ventricular fibrillation, inappropriately shocked, or indeterminate.

* * * * *